US010780150B2

(12) United States Patent
Krauss et al.

(10) Patent No.: US 10,780,150 B2
(45) Date of Patent: Sep. 22, 2020

(54) GLYCOSYLATED OLIGONUCLEOTIDES THAT MIMIC THE HIV-1 EPITOPE OF NEUTRALIZING MONOCLONAL ANTIBODY 2G12

(71) Applicant: BRANDEIS UNIVERSITY, Waltham, MA (US)

(72) Inventors: Isaac J. Krauss, Waltham, MA (US); Joel Sebastian Temme, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 0 days.

(21) Appl. No.: 16/092,137

(22) PCT Filed: Apr. 6, 2017

(86) PCT No.: PCT/US2017/026354
§ 371 (c)(1),
(2) Date: Oct. 8, 2018

(87) PCT Pub. No.: WO2017/176999
PCT Pub. Date: Oct. 12, 2017

(65) Prior Publication Data
US 2019/0117748 A1    Apr. 25, 2019

Related U.S. Application Data

(60) Provisional application No. 62/319,763, filed on Apr. 7, 2016.

(51) Int. Cl.
| | |
|---|---|
| *A61K 39/00* | (2006.01) |
| *C07H 21/04* | (2006.01) |
| *C07K 16/10* | (2006.01) |
| *A61K 39/395* | (2006.01) |
| *A61K 48/00* | (2006.01) |
| *C07H 15/22* | (2006.01) |
| *C12N 15/115* | (2010.01) |
| *C12N 15/10* | (2006.01) |
| *A61P 31/18* | (2006.01) |
| *A61K 39/39* | (2006.01) |
| *C12N 15/117* | (2010.01) |

(52) U.S. Cl.
CPC .......... *A61K 39/0005* (2013.01); *A61K 39/39* (2013.01); *A61P 31/18* (2018.01); *C07H 15/22* (2013.01); *C07H 21/04* (2013.01); *C12N 15/10* (2013.01); *C12N 15/115* (2013.01); *C12N 15/117* (2013.01); *A61K 2039/51* (2013.01); *A61K 2039/545* (2013.01); *C12N 2310/13* (2013.01); *C12N 2310/16* (2013.01); *C12N 2310/351* (2013.01); *C12N 2320/30* (2013.01)

(58) Field of Classification Search
CPC .. C07K 14/765; C07K 14/76; C07K 2319/00; C12N 15/62; A61K 48/00
See application file for complete search history.

(56) References Cited

U.S. PATENT DOCUMENTS

| | | |
|---|---|---|
| 2013/0116417 A1 | 5/2013 | Krauss et al. |
| 2016/0051690 A1 | 2/2016 | Krauss et al. |
| 2016/0304628 A1 | 10/2016 | Krauss et al. |
| 2016/0304858 A1 | 10/2016 | Krauss et al. |
| 2016/0304874 A1 | 10/2016 | Krauss |

FOREIGN PATENT DOCUMENTS

| | | |
|---|---|---|
| WO | 2011/156690 A1 | 12/2011 |
| WO | 2015/084846 A1 | 6/2015 |
| WO | WO2015084846 * | 6/2015 |
| WO | 2015/084861 A1 | 6/2016 |
| WO | 2015/084867 A1 | 6/2016 |

OTHER PUBLICATIONS

Temme et al., "Directed Evolution of 2G-12-Targeted Nonamannose Glycoclusters by SELMA," Chemistry 19:1-10 (2013).
Horiya et al., "Directed Evolution of Multivalent Glycopeptides Tightly Recognized by HIV Antibody 2G12," JACS 136:5407-5415 (2014).
PCT International Search Report and Written Opinion for corresponding PCT/US2017/026354 dated Aug. 29, 2017.

* cited by examiner

*Primary Examiner* — Barry A Chestnut
(74) *Attorney, Agent, or Firm* — Troutman Pepper Hamilton Sanders LLP (Rochester)

(57) ABSTRACT

Disclosed are oligonucleotides that binds specifically to HIV neutralizing monoclonal antibody 2G12 with a $K_4$ value lower than 20 nM, the oligonucleotide comprising a predicted structure, at 37° C., having exactly one stem-loop whereby the loop comprises the nucleotide sequence of AACCNACGGANAAA (SEQ ID NO: 1), where N is a modified nucleoside base, and the stem includes at least 3 nucleotide base-pairs and one of the nucleotides in the stem includes a modified nucleoside base, wherein the modified nucleoside base has the structure -B-L-A where A is a branched-chain $Man_9$ oligosaccharide, L is a linker molecule, and B is independently a pyrimidine or pyridine base linked to the sugar-phosphate backbone of the oligonucleotide. Immunogenic conjugates that include the oligonucleotide, and pharmaceutical compositions that include the oligonucleotide or the immunogenic conjugate are also disclosed. Various method of using the oligonucleotides, immunogenic conjugates, and pharmaceutical compositions are also disclosed.

21 Claims, 9 Drawing Sheets
Specification includes a Sequence Listing.

SEQUENCE LISTING

<160> NUMBER OF SEQ ID NOS: 34

<210> SEQ ID NO 1
<211> LENGTH: 14
<212> TYPE: DNA
<213> ORGANISM: Artificial Sequence
<220> FEATURE:
<223> OTHER INFORMATION: HIV-1 2G12 aptamer, clone 1 loop sequence
<220> FEATURE:
<221> NAME/KEY: misc_feature
<222> LOCATION: (5)..(5)
<223> OTHER INFORMATION: N at position 5 is a Mannose(9)-derivatized deoxyribosyl uridine
<220> FEATURE:
<221> NAME/KEY: misc_feature
<222> LOCATION: (11)..(11)
<223> OTHER INFORMATION: N at position 11 is a Mannose(9)-derivatized deoxyribosyl uridine

<400> SEQUENCE: 1
aaccnacgga naaa                                                    14

<210> SEQ ID NO 2
<211> LENGTH: 33
<212> TYPE: DNA
<213> ORGANISM: Artificial Sequence
<220> FEATURE:
<223> OTHER INFORMATION: HIV-1 2G12 aptamer E1
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 2
agacccacgg ngcaaccnac gganaaagca ccg                                33

<210> SEQ ID NO 3
<211> LENGTH: 26
<212> TYPE: DNA
<213> ORGANISM: Artificial Sequence
<220> FEATURE:
<223> OTHER INFORMATION: HIV-1 2G12 aptamer E1 fragment
<220> FEATURE:
<221> NAME/KEY: misc_feature
<222> LOCATION: (4)..(4)
<223> OTHER INFORMATION: N at position 4 is a Mannose(9)-derivatized
      deoxyribosyl uridine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (17)..(17)
<223> OTHER INFORMATION: N at position 17 is a Mannose(9)-derivatized
      deoxyribosyl uridine

<400> SEQUENCE: 3
cggngcaacc nacgganaaa gcaccg                                        26

<210> SEQ ID NO 4
<211> LENGTH: 36
<212> TYPE: DNA
<213> ORGANISM: Artificial Sequence
<220> FEATURE:
<223> OTHER INFORMATION: HIV-1 2G12 aptamer E2
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 4 agacccctcgg ngcaaccnac gganaaagca ccgagg          36

<210> SEQ ID NO 5
<211> LENGTH: 32
<212> TYPE: DNA
<213> ORGANISM: Artificial Sequence
<220> FEATURE:
<223> OTHER INFORMATION: HIV-1 2G12 aptamer E2 fragment
<220> FEATURE:
<221> NAME/KEY: misc_feature
<222> LOCATION: (7)..(7)
<223> OTHER INFORMATION: N at position 7 is a Mannose(9)-derivatized
      deoxyribosyl uridine
<220> FEATURE:
<221> NAME/KEY: misc_feature
<222> LOCATION: (14)..(14)
<223> OTHER INFORMATION: N at position 14 is a Mannose(9)-derivatized
      deoxyribosyl uridine
<220> FEATURE:
<221> NAME/KEY: misc_feature
<222> LOCATION: (20)..(20)
<223> OTHER INFORMATION: N at position 20 is a Mannose(9)-derivatized
      deoxyribosyl uridine

<400> SEQUENCE: 5
cctcggngca accnacggan aaagcaccga gg          32

<210> SEQ ID NO 6
<211> LENGTH: 40
<212> TYPE: DNA
<213> ORGANISM: Artificial Sequence
<220> FEATURE:
<223> OTHER INFORMATION: HIV-1 2G12 aptamer E3
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 6
tgtccctcgg ngcaaccnac gganaaagca ccgagggaca          40

<210> SEQ ID NO 7
<211> LENGTH: 56
<212> TYPE: DNA
<213> ORGANISM: Artificial Sequence
<220> FEATURE:
<223> OTHER INFORMATION: HIV-1 2G12 aptamer, clone 1
<220> FEATURE:
<221> NAME/KEY: misc_feature
<222> LOCATION: (21)..(21)
<223> OTHER INFORMATION: N at position 21 is a Mannose(9)-derivatized
 deoxyribosyl uridine
<220> FEATURE:
<221> NAME/KEY: misc_feature
<222> LOCATION: (28)..(28)
<223> OTHER INFORMATION: N at position 28 is a Mannose(9)-derivatized
      deoxyribosyl uridine
<220> FEATURE:
<221> NAME/KEY: misc_feature
<222> LOCATION: (34)..(34)
<223> OTHER INFORMATION: N at position 34 is a Mannose(9)-derivatized
      deoxyribosyl uridine

<400> SEQUENCE: 7
cgggtacggg agacccacgg ngcaaccnac gganaaagca cacaggagac gacaag        56

<210> SEQ ID NO 8
<211> LENGTH: 46
<212> TYPE: DNA
<213> ORGANISM: Artificial Sequence
<220> FEATURE:
<223> OTHER INFORMATION: minimized HIV-1 2G12 aptamer, clone 1-B
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 8
agacccacgg ngcaaccnac gganaaagca cacaggagac gacaag        46

<210> SEQ ID NO 9
<211> LENGTH: 35
<212> TYPE: DNA
<213> ORGANISM: Artificial Sequence
<220> FEATURE:
<223> OTHER INFORMATION: minimized HIV-1 2G12 aptamer, clone 1-C
<220> FEATURE:
<221> NAME/KEY: misc_feature
<222> LOCATION: (21)..(21)
<223> OTHER INFORMATION: N at position 21 is a Mannose(9)-derivatized
      deoxyribosyl uridine
<220> FEATURE:
<221> NAME/KEY: misc_feature
<222> LOCATION: (28)..(28)
<223> OTHER INFORMATION: N at position 28 is a Mannose(9)-derivatized
      deoxyribosyl uridine
<220> FEATURE:
<221> NAME/KEY: misc_feature
<222> LOCATION: (34)..(34)
<223> OTHER INFORMATION: N at position 34 is a Mannose(9)-derivatized
      deoxyribosyl uridine

<400> SEQUENCE: 9
cgggtacggg agacccacgg ngcaaccnac ggana        35

<210> SEQ ID NO 10
<211> LENGTH: 25
<212> TYPE: DNA
<213> ORGANISM: Artificial Sequence
<220> FEATURE:
<223> OTHER INFORMATION: minimized HIV-1 2G12 aptamer, clone 1-D
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized deoxyribosyl uridine

<400> SEQUENCE: 10
agacccacgg ngcaaccnac ggana                                         25

<210> SEQ ID NO 11
<211> LENGTH: 33
<212> TYPE: DNA
<213> ORGANISM: Artificial Sequence
<220> FEATURE:
<223> OTHER INFORMATION: truncated HIV-1 2G12 aptamer, clone T1
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 11
agacccacgg ngcaaccnac gganaaagca cac                                33

<210> SEQ ID NO 12
<211> LENGTH: 38
<212> TYPE: DNA
<213> ORGANISM: Artificial Sequence
<220> FEATURE:
<223> OTHER INFORMATION: truncated HIV-1 2G12 aptamer, clone T2
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 12
agacccacgg ngcaaccnac gganaaagca cacaggag                           38

<210> SEQ ID NO 13
<211> LENGTH: 43
<212> TYPE: DNA
<213> ORGANISM: Artificial Sequence
<220> FEATURE:
<223> OTHER INFORMATION: truncated HIV-1 2G12 aptamer, clone T3
<220> FEATURE:
<221> NAME/KEY: misc_feature
<222> LOCATION: (21)..(21)
<223> OTHER INFORMATION: N at position 21 is a Mannose(9)-derivatized
      deoxyribosyl uridine
<220> FEATURE:
<221> NAME/KEY: misc_feature
<222> LOCATION: (28)..(28)
<223> OTHER INFORMATION: N at position 28 is a Mannose(9)-derivatized
      deoxyribosyl uridine
<220> FEATURE:
<221> NAME/KEY: misc_feature

```
<222> LOCATION: (34)..(34)
<223> OTHER INFORMATION: N at position 34 is a Mannose(9)-derivatized
      deoxyribosyl uridine

<400> SEQUENCE: 13
cgggtacggg agacccacgg ngcaaccnac gganaaagca cac                              43

<210> SEQ ID NO 14
<211> LENGTH: 48
<212> TYPE: DNA
<213> ORGANISM: Artificial Sequence
<220> FEATURE:
<223> OTHER INFORMATION: truncated HIV-1 2G12 aptamer, clone T4
<220> FEATURE:
<221> NAME/KEY: misc_feature
<222> LOCATION: (21)..(21)
<223> OTHER INFORMATION: N at position 21 is a Mannose(9)-derivatized
      deoxyribosyl uridine
<220> FEATURE:
<221> NAME/KEY: misc_feature
<222> LOCATION: (28)..(28)
<223> OTHER INFORMATION: N at position 28 is a Mannose(9)-derivatized
      deoxyribosyl uridine
<220> FEATURE:
<221> NAME/KEY: misc_feature
<222> LOCATION: (34)..(34)
<223> OTHER INFORMATION: N at position 34 is a Mannose(9)-derivatized
      deoxyribosyl uridine

<400> SEQUENCE: 14
cgggtacggg agacccacgg ngcaaccnac gganaaagca cacaggag                         48

<210> SEQ ID NO 15
<211> LENGTH: 25
<212> TYPE: DNA
<213> ORGANISM: Artificial Sequence
<220> FEATURE:
<223> OTHER INFORMATION: HIV-1 2G12 aptamer, clone 2 partial sequence
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 15
agacccacag ngcaaccnac ggana                                                  25

<210> SEQ ID NO 16
<211> LENGTH: 33
<212> TYPE: DNA
<213> ORGANISM: Artificial Sequence
<220> FEATURE:
<223> OTHER INFORMATION: HIV-1 2G12 aptamer, clone E1-M1
<220> FEATURE:
<221> NAME/KEY: misc_feature
<222> LOCATION: (1)..(1)
<223> OTHER INFORMATION: N at position 1 is 2'-methoxy deoxyribosyl
      adenosine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
```

```
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 16
ngacccacgg ngcaaccnac gganaaagca ccg                                    33

<210> SEQ ID NO 17
<211> LENGTH: 33
<212> TYPE: DNA
<213> ORGANISM: Artificial Sequence
<220> FEATURE:
<223> OTHER INFORMATION: HIV-1 2G12 aptamer, clone E1-M2
<220> FEATURE:
<221> NAME/KEY: misc_feature
<222> LOCATION: (2)..(2)
<223> OTHER INFORMATION: N at position 2 is 2'-methoxy deoxyribosyl
      guanosine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 17
anacccacgg ngcaaccnac gganaaagca ccg                                    33

<210> SEQ ID NO 18
<211> LENGTH: 33
<212> TYPE: DNA
<213> ORGANISM: Artificial Sequence
<220> FEATURE:
<223> OTHER INFORMATION: HIV-1 2G12 aptamer, clone E1-M3
<220> FEATURE:
<221> NAME/KEY: misc_feature
<222> LOCATION: (3)..(3)
<223> OTHER INFORMATION: N at position 3 is 2'-methoxy deoxyribosyl
      adenosine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 18
agncccacgg ngcaaccnac gganaaagca ccg                                    33
```

```
<210> SEQ ID NO 19
<211> LENGTH: 33
<212> TYPE: DNA
<213> ORGANISM: Artificial Sequence
<220> FEATURE:
<223> OTHER INFORMATION: HIV-1 2G12 aptamer, clone E1-M4
<220> FEATURE:
<221> NAME/KEY: misc_feature
<222> LOCATION: (7)..(7)
<223> OTHER INFORMATION: N at position 7 is 2'-methoxy deoxyribosyl
      adenosine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 19
agacccncgg ngcaaccnac gganaaagca ccg                                33

<210> SEQ ID NO 20
<211> LENGTH: 33
<212> TYPE: DNA
<213> ORGANISM: Artificial Sequence
<220> FEATURE:
<223> OTHER INFORMATION: HIV-1 2G12 aptamer, clone E1-M5
<220> FEATURE:
<221> NAME/KEY: misc_feature
<222> LOCATION: (9)..(9)
<223> OTHER INFORMATION: N at position 9 is 2'-methoxy deoxyribosyl
      guanosine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 20
agacccacng ngcaaccnac gganaaagca ccg                                33

<210> SEQ ID NO 21
<211> LENGTH: 33
<212> TYPE: DNA
<213> ORGANISM: Artificial Sequence
<220> FEATURE:
<223> OTHER INFORMATION: HIV-1 2G12 aptamer, clone E1-M6
<220> FEATURE:
<221> NAME/KEY: misc_feature
<222> LOCATION: (10)..(10)
<223> OTHER INFORMATION: N at position 10 is 2'-methoxy deoxyribosyl
      guanosine
<220> FEATURE:
<221> NAME/KEY: misc_feature
<222> LOCATION: (11)..(11)
```

```
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 21
agacccacgn ngcaaccnac gganaaagca ccg                               33

<210> SEQ ID NO 22
<211> LENGTH: 33
<212> TYPE: DNA
<213> ORGANISM: Artificial Sequence
<220> FEATURE:
<223> OTHER INFORMATION: HIV-1 2G12 aptamer, clone E1-M7
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (12)..(12)
<223> OTHER INFORMATION: N at position 12 is 2'-methoxy deoxyribosyl
      guanosine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 22
agacccacgg nncaaccnac gganaaagca ccg                               33

<210> SEQ ID NO 23
<211> LENGTH: 33
<212> TYPE: DNA
<213> ORGANISM: Artificial Sequence
<220> FEATURE:
<223> OTHER INFORMATION: HIV-1 2G12 aptamer, clone E1-M8
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (14)..(14)
<223> OTHER INFORMATION: N at position 14 is 2'-methoxy deoxyribosyl
      adenosine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 23
```
agacccacgg ngcnaccnac gganaaagca ccg                                    33

<210> SEQ ID NO 24
<211> LENGTH: 33
<212> TYPE: DNA
<213> ORGANISM: Artificial Sequence
<220> FEATURE:
<223> OTHER INFORMATION: HIV-1 2G12 aptamer, clone E1-M9
<220> FEATURE:
<221> NAME/KEY: misc_feature
<222> LOCATION: (11)..(11)
<223> OTHER INFORMATION: N at position 11 ia a Mannose(9)-derivatized
      deoxyribosyl uridine
<220> FEATURE:
<221> NAME/KEY: misc_feature
<222> LOCATION: (15)..(15)
<223> OTHER INFORMATION: N at position 15 ia 2'-methoxy deoxyribosyl
      adenosine
<220> FEATURE:
<221> NAME/KEY: misc_feature
<222> LOCATION: (18)..(18)
<223> OTHER INFORMATION: N at position 18 ia a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 ia a Mannose(9)-derivatized
      deoxyribosyl uridine

<400> SEQUENCE: 24
agacccacgg ngcanccnac gganaaagca ccg                                    33

<210> SEQ ID NO 25
<211> LENGTH: 33
<212> TYPE: DNA
<213> ORGANISM: Artificial Sequence
<220> FEATURE:
<223> OTHER INFORMATION: HIV-1 2G12 aptamer, clone E1-M10
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (19)..(19)
<223> OTHER INFORMATION: N at position 19 is 2'-methoxy deoxyribosyl
      adenosine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 25
agacccacgg ngcaaccnnc gganaaagca ccg                                    33

<210> SEQ ID NO 26
<211> LENGTH: 33
<212> TYPE: DNA
<213> ORGANISM: Artificial Sequence
<220> FEATURE:
<223> OTHER INFORMATION: HIV-1 2G12 aptamer, clone E1-M11
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:

```
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (21)..(21)
<223> OTHER INFORMATION: N at position 21 is 2'-methoxy deoxyribosyl
      guanosine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 26
agacccacgg ngcaaccnac nganaaagca ccg                                    33

<210> SEQ ID NO 27
<211> LENGTH: 33
<212> TYPE: DNA
<213> ORGANISM: Artificial Sequence
<220> FEATURE:
<223> OTHER INFORMATION: HIV-1 2G12 aptamer, clone E1-M12
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (22)..(22)
<223> OTHER INFORMATION: N at position 22 is 2'-methoxy deoxyribosyl
      guanosine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine

<400> SEQUENCE: 27
agacccacgg ngcaaccnac gnanaaagca ccg                                    33

<210> SEQ ID NO 28
<211> LENGTH: 33
<212> TYPE: DNA
<213> ORGANISM: Artificial Sequence
<220> FEATURE:
<223> OTHER INFORMATION: HIV-1 2G12 aptamer, clone E1-M13
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (23)..(23)
<223> OTHER INFORMATION: N at position 23 is 2'-methoxy deoxyribosyl
      adenosine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine
```

<400> SEQUENCE: 28
agacccacgg ngcaaccnac ggnnaaagca ccg                                33

<210> SEQ ID NO 29
<211> LENGTH: 33
<212> TYPE: DNA
<213> ORGANISM: Artificial Sequence
<220> FEATURE:
<223> OTHER INFORMATION: HIV-1 2G12 aptamer, clone E1-M14
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine
<220> FEATURE:
<221> NAME/KEY: misc_feature
<222> LOCATION: (25)..(25)
<223> OTHER INFORMATION: N at position 25 is 2'-methoxy deoxyribosyl
      adenosine

<400> SEQUENCE: 29
agacccacgg ngcaaccnac ggannaagca ccg                                33

<210> SEQ ID NO 30
<211> LENGTH: 33
<212> TYPE: DNA
<213> ORGANISM: Artificial Sequence
<220> FEATURE:
<223> OTHER INFORMATION: 2'-methoxy deoxyribosyl adenosine
<220> FEATURE:
<221> NAME/KEY: misc_feature
<222> LOCATION: (11)..(11)
<223> OTHER INFORMATION: N at position 11 is a Mannose(9)-derivatized
      deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
      deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
      deoxyribosyl uridine
<220> FEATURE:
<221> NAME/KEY: misc_feature
<222> LOCATION: (26)..(26)
<223> OTHER INFORMATION: N at position 26 is a 2'-methoxy deoxyribosyl
      adenosine

<400> SEQUENCE: 30
agacccacgg ngcaaccnac ggananagca ccg                                33

<210> SEQ ID NO 31
<211> LENGTH: 33
<212> TYPE: DNA
<213> ORGANISM: Artificial Sequence
<220> FEATURE:
<223> OTHER INFORMATION: HIV-1 2G12 aptamer, clone E1-M16
<220> FEATURE:
<221> NAME/KEY: misc_feature
<222> LOCATION: (11)..(11)
<223> OTHER INFORMATION: N at position 11 is a Mannose(9)-derivatized

```
       deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
       deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
       deoxyribosyl uridine
<220> FEATURE:
<221> NAME/KEY: misc_feature
<222> LOCATION: (27)..(27)
<223> OTHER INFORMATION: N at position 27 is 2'-methoxy deoxyribosyl
       adenosine

<400> SEQUENCE: 31
agacccacgg ngcaaccnac gganaangca ccg                                    33

<210> SEQ ID NO 32
<211> LENGTH: 33
<212> TYPE: DNA
<213> ORGANISM: Artificial Sequence
<220> FEATURE:
<223> OTHER INFORMATION: HIV-1 2G12 aptamer, clone E1-M17
<220> FEATURE:
<221> NAME/KEY: misc_feature
<222> LOCATION: (11)..(11)
<223> OTHER INFORMATION: N at position 11 is a Mannose(9)-derivatized
       deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
       deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
       deoxyribosyl uridine
<220> FEATURE:
<221> NAME/KEY: misc_feature
<222> LOCATION: (28)..(28)
<223> OTHER INFORMATION: N at position 28 is a 2'-methoxy deoxyribosyl
       guanosine

<400> SEQUENCE: 32
agacccacgg ngcaaccnac gganaaanca ccg                                    33

<210> SEQ ID NO 33
<211> LENGTH: 33
<212> TYPE: DNA
<213> ORGANISM: Artificial Sequence
<220> FEATURE:
<223> OTHER INFORMATION: HIV-1 2G12 aptamer, clone E1-M18
<220> FEATURE:
<221> NAME/KEY: misc_feature
<222> LOCATION: (11)..(11)
<223> OTHER INFORMATION: N at position 11 is a Mannose(9)-derivatized
       deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized
       deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized
       deoxyribosyl uridine
<220> FEATURE:
<221> NAME/KEY: misc_feature
<222> LOCATION: (30)..(30)
<223> OTHER INFORMATION: N at position 30 is a 2'-methoxy deoxyribosyl
```

-continued adenosine

<400> SEQUENCE: 33
agacccacgg ngcaaccnac gganaaagcn ccg 33

<210> SEQ ID NO 34
<211> LENGTH: 33
<212> TYPE: DNA
<213> ORGANISM: Artificial Sequence
<220> FEATURE:
<223> OTHER INFORMATION: HIV-1 2G12 aptamer, clone E1-M19
<220> FEATURE:
<221> NAME/KEY: misc_feature
<222> LOCATION: (11)..(11)
<223> OTHER INFORMATION: N at position 11 is a Mannose(9)-derivatized deoxyribosyl uridine
<220> FEATURE:
<221> NAME/KEY: misc_feature
<222> LOCATION: (18)..(18)
<223> OTHER INFORMATION: N at position 18 is a Mannose(9)-derivatized deoxyribosyl uridine
<220> FEATURE:
<221> NAME/KEY: misc_feature
<222> LOCATION: (24)..(24)
<223> OTHER INFORMATION: N at position 24 is a Mannose(9)-derivatized deoxyribosyl uridine
<220> FEATURE:
<221> NAME/KEY: misc_feature
<222> LOCATION: (33)..(33)
<223> OTHER INFORMATION: N at position 33 is 2'-methoxy deoxyribosyl guanosine

<400> SEQUENCE: 34
agacccacgg ngcaaccnac gganaaagca ccn 33

GLYCOSYLATED OLIGONUCLEOTIDES THAT MIMIC THE HIV-1 EPITOPE OF NEUTRALIZING MONOCLONAL ANTIBODY 2G12

This application is a national stage application under 35 U.S.C. § 371 of PCT Application No. PCT/US2017/026354, filed Apr. 6, 2017, which claims the benefit of U.S. Provisional Patent Application Ser. No. 62/121,237, filed Feb. 26, 2015, which is hereby incorporated by reference in its entirety.

This invention was made with government support under Grant No. R01 AI090745 awarded by the National Institutes of Health. The government has certain rights in the invention.

FIELD OF THE INVENTION

The present invention relates to high temperature selection of nucleotide-supported carbohydrate vaccines, glycosylated oligonucleotides that bind to carbohydrate-binding monoclonal antibodies with high affinity, immunogenic conjugates and pharmaceutical compositions containing the same, and their use to induce immune responses against the same.

BACKGROUND OF THE INVENTION

Monoclonal antibody 2G12, isolated from HIV+ patient serum in 1996, neutralizes a broad range of HIV isolates and has been shown to be protective in animal models of HIV infection. 2G12 binds to a cluster of high-mannose ($Man_{5-9}GlcNAc_2$) glycans on HIV envelope protein gp120, and synthetic glycoclusters which closely mimic this epitope are of interest as immunogens which may be able to elicit a 2G12-like antibody response through vaccination.

There have been many attempts to design clusters of oligomannose glycans that mimic the 2G12 epitope. Chemical synthesis has enabled construction of well-defined structures in which glycans are mounted on numerous backbones, including cyclic peptides, PNA, dendrimers, and Qβ phage particles. Additionally, yeast strains have been engineered to express primarily high mannose carbohydrates on their surface. Unfortunately, none of these immunogens has been used successfully to raise a 2G12-like antibody response in vivo. In the best cases, when mannose-binding antibodies have been generated, their binding to gp120 or neutralization of HIV in vitro has still been weak or undetectable. Among several reasons for these failures is the likelihood that the clustering of oligomannose carbohydrates present in these immunogens did not sufficiently resemble the 2G12 epitope.

Optimized clustering of carbohydrates for more faithful mimicry of the 2G12 epitope was explored by using the antibody to recognize and select the best gp120 mimics from among a very diverse library. A new selection method, termed SELMA (SELection with Modified Aptamers), uses diverse DNA backbones to cluster the glycans in various ways (U.S. Patent Application Publ. No. 20130116417; MacPherson et al., *Angew. Chem. Int. Ed.* 50:11238-11242 (2011)). Libraries were constructed using copper assisted alkyne/azide cycloaddition (CuAAAC) chemistry to attach glycans to a library of random DNA sequences containing alkynyl bases. In single-stranded form, each DNA sequence clusters the glycans in a unique geometry, and the clusters that were selected from the library by binding to the target lectin (2G12 in this case) were amplified by PCR to generate a new library for further selection. The process was then repeated for several cycles with increasingly stringent selection conditions. By this method, clusters of 5-10 oligomannose glycans that were moderately good mimics of the 2G12 epitope were obtained; these constructs were recognized by 2G12 with 150-500 nM $K_d$'s. However, the HIV envelope protein, gp120, is recognized much more tightly, with a $K_d$ of ~6-9 nM. To generate gp120 mimics that more faithfully replicate the glycan epitope, it will be necessary to generate glycan-oligonucleotides that are capable of binding to neutralizing monoclonal antibodies, like 2G12, with an affinity that is substantially the same as or less than that of the gp120-2G12 interaction. Therefore, methods of developing better epitope mimics are needed.

The present invention is directed to overcoming these and other deficiencies in the art.

SUMMARY OF THE INVENTION

A first aspect of the present invention relates to an oligonucleotide that binds specifically to HIV neutralizing monoclonal antibody 2G12 with a $K_d$ value that is lower than 20 nM, the oligonucleotide comprising a predicted structure, at 37° C., having exactly one stem-loop whereby the loop comprises the nucleotide sequence of AACC<u>N</u>ACGGA<u>N</u>AAA (SEQ ID NO: 1), where <u>N</u> is a modified nucleoside base, and the stem includes at least 3 nucleotide base-pairs and one of the nucleotides in the stem includes a modified nucleoside base, wherein the modified nucleoside base has the structure

-B-L-A where
   A is a branched-chain $Man_9$ oligosaccharide,
   L is a linker molecule, and
   B is independently a pyrimidine or pyridine base linked to the sugar-phosphate backbone of the oligonucleotide.

Exemplary oligonucleotides according to the first aspect of the invention include, without limitation,

| Name | Sequence | SEQ ID NO: |
|---|---|---|
| E1 | AGACCCACGG<u>N</u>GCAACC<u>N</u>ACGGA<u>N</u>AAAGCACCG | 2 |
| E1 (nt 8-33) | CGG<u>N</u>GCAACC<u>N</u>ACGGA<u>N</u>AAAGCACCG | 3 |
| E2 | AGACCCTCGG<u>N</u>GCAACC<u>N</u>ACGGA<u>N</u>AAAGCACCGAGG | 4 |
| E2 (nt 5-36) | CCTCGG<u>N</u>GCAACC<u>N</u>ACGGA<u>N</u>AAAGCACCGAGG | 5 |
| E3 | TGTCCCTCGG<u>N</u>GCAACC<u>N</u>ACGGA<u>N</u>AAAGCACCGAGGGACA | 6 |

A second aspect of the invention relates to an immunogenic conjugate that includes an oligonucleotide according to the first aspect of the invention covalently or non-covalently bound to an immunogenic carrier molecule.

A third aspect of the invention relates to a pharmaceutical composition that includes a pharmaceutically acceptable carrier and an oligonucleotide according to the first aspect of the invention or an immunogenic conjugate according to the second aspect of the invention.

A fourth aspect of the present invention relates to a method of inducing an immune response in an individual that includes administering to an individual an oligonucleotide according to the first aspect of the invention, an immunogenic conjugate according to the second aspect of the invention, or a pharmaceutical composition according to the third aspect of the invention, where the step of administering is effective to induce an immune response against the oligonucleotide.

A fifth aspect of the present invention relates to a method of inhibiting HIV-1 infection or proliferation that includes administering to an individual an oligonucleotide according to the first aspect of the invention, an immunogenic conjugate according to the second aspect of the invention, or a pharmaceutical composition according to the third aspect of the invention, wherein the step of administering is effective to induce a neutralizing immune response against HIV-1.

A sixth aspect of the present invention relates to a method for detecting a neutralizing antibody in serum that includes providing an oligonucleotide according to the first aspect of the invention, contacting the oligonucleotide with serum from an individual, and detecting whether the oligonucleotide binds specifically to an antibody present in the serum, where the detecting step is carried out using a label.

The accompanying Examples demonstrate that a modification to the SELMA procedure described in U.S. Patent Application Publ. No. 20130116417, which is hereby incorporated by reference in its entirety, achieves dramatically improved results insofar as the procedure selects for structurally distinct glycosylated oligonucleotides that exhibit substantially higher affinity to the selection target. The oligonucleotides identified in the accompanying Examples contain 3 glycosylation sites and very tightly recognized 2G12, with Kd's less than 20 nM. This contrasts with the average of ~8 glycosylation sites resulting from the analogous selection procedure of U.S. Patent Application Publ. No. 20130116417, whereby the selected oligonucleotides exhibited ~300 nM Kd's against 2G12. This tight recognition displayed by the glycosylated oligonucleotides of the present invention is significant in that it is comparable to the strength of the interaction between 2G12 and the HIV envelope protein gp120 (Hoorelbeke et al., *FEBS Lett.* 587:860-866 (2013), which is hereby incorporated by reference in its entirety). Structural modifications introduced into Clone 1 (SEQ ID NO: 7, FIG. 1A) allowed for elimination of extraneous nucleotides, while maintaining structurally important features. The glycosylated oligonucleotides defined herein are characterized by a single stem/loop structure, and possess both a low Kd value (less than 20 nM) and an $Fb_{max}$ value exceeding, in some instances, 70 percent.

BRIEF DESCRIPTION OF THE DRAWINGS

FIG. 1E illustrates the gel purification of the truncations illustrated in FIGS. 1B-1D. Lanes 1-3 are unpurified truncations (FIGS. 1B-1D, respectively), and lanes 4-6 are purified truncations (FIGS. 1B-1D, respectively). FIG. 1F is a graph depicting the results of a filter-binding study comparing the truncations to the full length clone.

DETAILED DESCRIPTION OF THE INVENTION

Figure 1A:
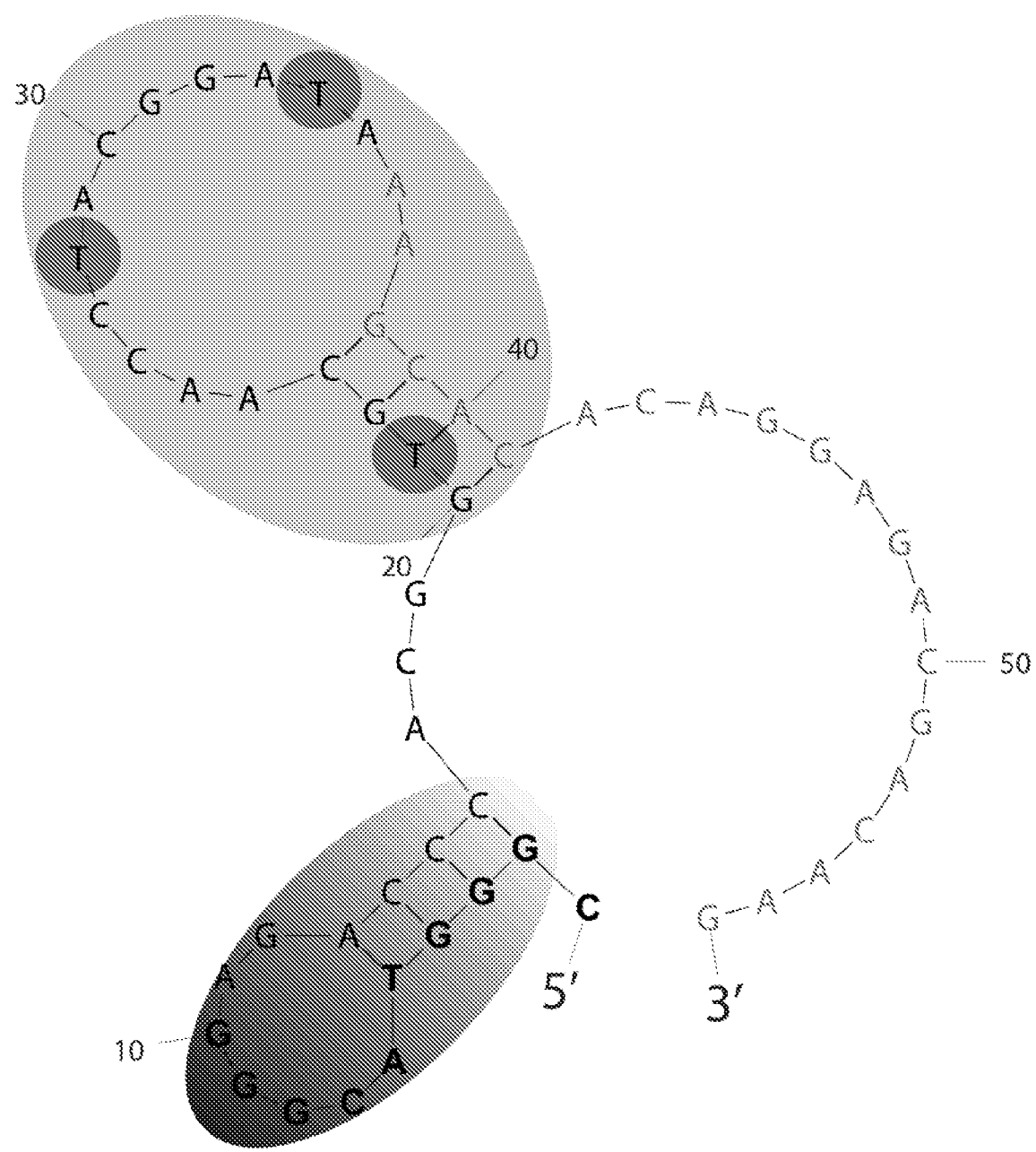
FIGS. 1A-F illustrate the mFold analysis and 2G12 binding of 37° C. Clone 1 truncations. mFold predicted secondary structures of Clone 1 and several of its variants are shown in FIGS. 1A-D as follows: Full length Clone 1 (1A, SEQ ID NO: 7); Clone 1 stem region truncation (1B, SEQ ID NO: 8); Clone 1 reverse primer truncation (1C, SEQ ID NO: 9); and Clone 1 stem and reverse primer truncations (1D, SEQ ID NO: 10). Stem region in bold text, random region in black text, and reverse primer region is in gray text. Glycosylation sites are highlighted by dark ovals. Suspected binding hairpin domain is highlighted by light gray oval. Stem region hairpin is highlighted by gradient oval.

The present invention relates to a method for in vitro selection of glycosylated oligonucleotides, which involves modification to the SELMA (SELection with Modified Aptamers) procedure described in U.S. Patent Application Publ. No. 20130116417, which is hereby incorporated by reference in its entirety, to achieve structurally and functionally distinct glycosylated oligonucleotides. Using this in vitro selection in combination with directed evolution, it is possible to develop binding partners with any of a variety of target proteins, including epitope mimics that are bound tightly and specifically by carbohydrate-specific monoclonal antibodies.

Accordingly, the method for selecting a glycosylated oligonucleotide that binds to a target protein includes providing a pool of modified, single-strand-double-strand hybrid oligonucleotides that are glycosylated within the single-strand region, combining the pool with a target protein to form a mixture, incubating the mixture at a temperature above 20° C. for a period of time sufficient to allow any target protein to bind one or more of the modified, single-strand-double-strand hybrid oligonucleotides, and isolating from the mixture the modified, single-strand-double-strand hybrid oligonucleotides that bind to the target protein, thereby identifying a plurality of selected oligonucleotides. Multiple rounds of selection and regenerating pools of modified, single-strand-double-strand hybrid oligonucleotides that are glycosylated within the single-strand region can be performed in the manner illustrated in PCT Application Publ. No. WO 2015/084846, which is hereby incorporated by reference in its entirety.

Briefly, one example of the SELMA procedure uses diverse DNA backbones to cluster the glycans in various ways (MacPherson et al., *Angew. Chem. Int. Ed.* 50:11238-11242 (2011); Temme et al., *Chem. Eur. J.* 19:17291-17295

(2013), which are hereby incorporated by reference in their entirety). The library is constructed using copper assisted alkyne/azide cycloaddition (CuAAAC) chemistry (Kolb et al., *Angew. Chem. Int. Ed.* 40:2004-2021 (2001); Rostovtsev et al., *Angew. Chem. Int. Ed.* 41:2596-2599 (2002); Gierlich et al., *Org. Lett.* 8:3639-3642 (2006); Gierlich et al., *Chem. Eur. J.* 13:9486-9494 (2007), which are hereby incorporated in their entirety) to attach glycans to a library of random DNA sequences containing alkynyl bases. In a single-stranded portion of the modified, single-strand-double-strand hybrid oligonucleotides, each DNA sequence clusters the glycans in a unique geometry, and the clusters which are selected from the library by binding to the target protein (HIV neutralizing monoclonal antibody 2G12, as illustrated) are amplified by PCR to generate a new library for further selection. The process is then repeated for several cycles with increasingly stringent selection conditions. Importantly, deviation from the prior SELMA approach involves higher stringency conditions during selection, which achieves a lower degree of glycosylation.

The provided pool of modified, single-strand-double-strand hybrid oligonucleotides that are glycosylated within the single-strand region is preferably large enough to afford sufficient diversity so as to allow for selection of multiple, diverse oligonucleotides that exhibit target protein binding capability. By way of example, the provided pool comprises about $10^{10}$ or greater, about $10^{11}$ or greater, about $10^{12}$ or greater, or about $10^{13}$ or greater modified, single-strand-double-strand hybrid oligonucleotides that are glycosylated within the single-strand region.

Creation of the first pool is carried out by first generating a library of single-stranded, hairpin-loop DNA structures of sufficient length to afford an oligonucleotide of the desired complexity. Each hairpin-loop structure includes a loop portion having a primer binding site (discussed infra) and a partial stem portion that includes a region at the 3' end hybridized to a complementary region displaced from the 5' end. Initially, the sequence between the complementary region and the 5' terminus includes a random sequence. This random sequence can be of any length suitable to afford introduction of one or more glycans, typically from about 15 to about 100 nucleobases in length, more preferably about 15 to about 60 nucleobases or about 20 to about 50 nucleobases in length.

In certain embodiments, the region containing the randomized sequence comprises from about 10% to about 20% adenine (A). Preferably, the randomized region comprises about 10%, about 11%, about 12%, about 13%, about 14%, about 15%, about 16%, about 17%, about 18%, about 19%, or about 20% adenine (A). More preferably, the randomized region comprises 15% adenine (A).

To facilitate glycosylation of the resulting oligonucleotide, the initial library is treated with a polymerase, dNTPs and modified dNTPs or modified rNTPs, under conditions effective to allow for extension of the 3' end using the sequence between the complementary region and the 5' terminus as a template. The resulting stem-loop nucleic acid includes a single strand containing one or more modified nucleosides (near the 3' end). Any nucleoside base that contains a reactive group suitable for click chemistry coupling of a compatibly modified monosaccharide or oligosaccharide to the oligonucleotide can be used during this extension step. Examples of modified nucleosides that can be introduced during this extension step include, without limitation, $N_6$-(6-azido)hexyl-dATP (Jena Bioscience), C8-alkyne-dCTP (Jena Bioscience), 5-ethynyl-dUTP (Jena Bioscience), C8-alkyne-dUTP (Jena Bioscience), 5-azido-$C_3$-UTP (Jena Bioscience), 5-ethynyl-UTP (Jena Bioscience), $N^6$-propargyl-ATP (Jena Bioscience), 2-ethynyl-ATP (Jena Bioscience), and 8-azido-ATP. As a consequence of introducing these modified nucleosides to form the 3' end extension, this portion of the strand, containing the one or more modified nucleosides, has one or more azido or alkynyl groups (alkenyl groups can also be used) available for click reaction.

The modified nucleosides can be located at adjacent positions (i.e., where one modified nucleosides is linked via the sugar-phosphate backbone to another modified nucleosides) or at nonadjacent positions (i.e., where no two modified nucleosides are linked via the sugar-phosphate backbone to one another). In certain embodiments, the resulting oligonucleotide includes a plurality of modified nucleosides, some of which are adjacent to one another and some of which are not adjacent to another modified nucleoside.

After introducing the modified nucleosides to the 3' extension, the one or more monosaccharides or oligosaccharides are attached using appropriate click chemistry reactions, which include thiol-ene reactions (reaction of a thiol bond across an alkene or alkyne by either a free radical or ionic mechanism) (see, e.g., Hoyle et al., *Angew. Chem. Int. Ed.* 49:1540-1573 (2010, which is hereby incorporated by reference in its entirety) as well as azide-alkyne cycloaddition reactions (reaction of an azido group with a terminal or internal alkyne) (see, e.g., Temme et al., *Chem. Eur. J.* 19:17291-17295 (2013) and Hong et al., Angew. Chem. Int. Ed. 48:9879-9883 (2009), which are hereby incorporated by reference in their entirety). Typically, copper catalysis or ruthenium catalysis or strain-promoted alkyne-azide cycloaddition is used.

The monosaccharide or oligosaccharide to be linked to the modified amino acid(s) of the polypeptide can be any saccharide modified with a click chemistry reactive group (e.g., thiol, azide, alkyne or alkene). Suitable monosaccharides include, without limitation, glucose, galactose, mannose, arabinose, fucose, rhamnose, sialic acid, and N-acetylglucosamine.

Suitable oligosaccharides include branched or unbranched oligosaccharide that include at least 3 saccharide moieties, typically from about 3 saccharide moieties up to about 20 saccharide moieties. The saccharide moieties include those identified as suitable monosaccharides.

Exemplary N-linked glycan structures include high mannose N-glycans present in the human lung:

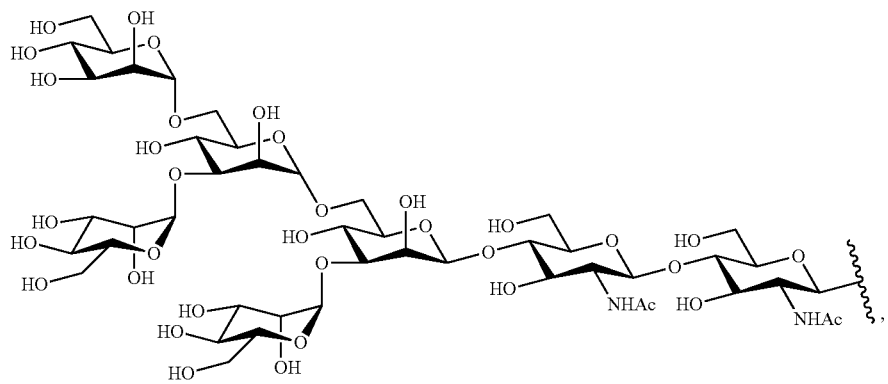

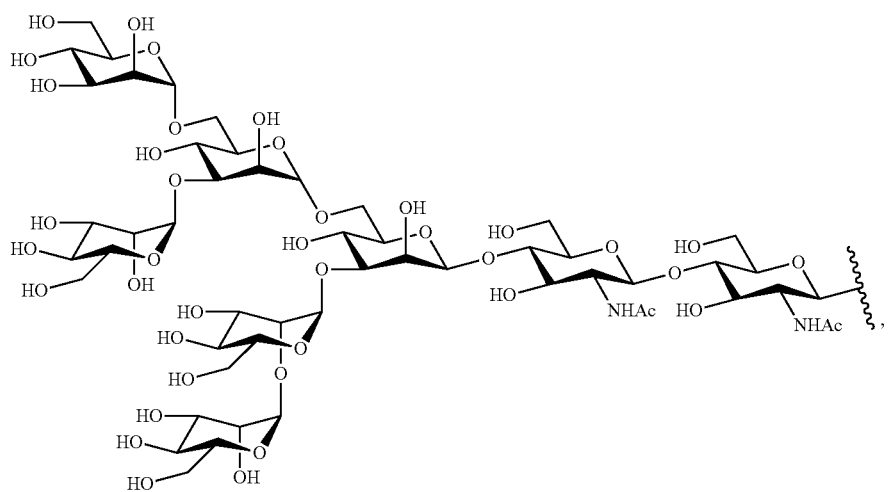

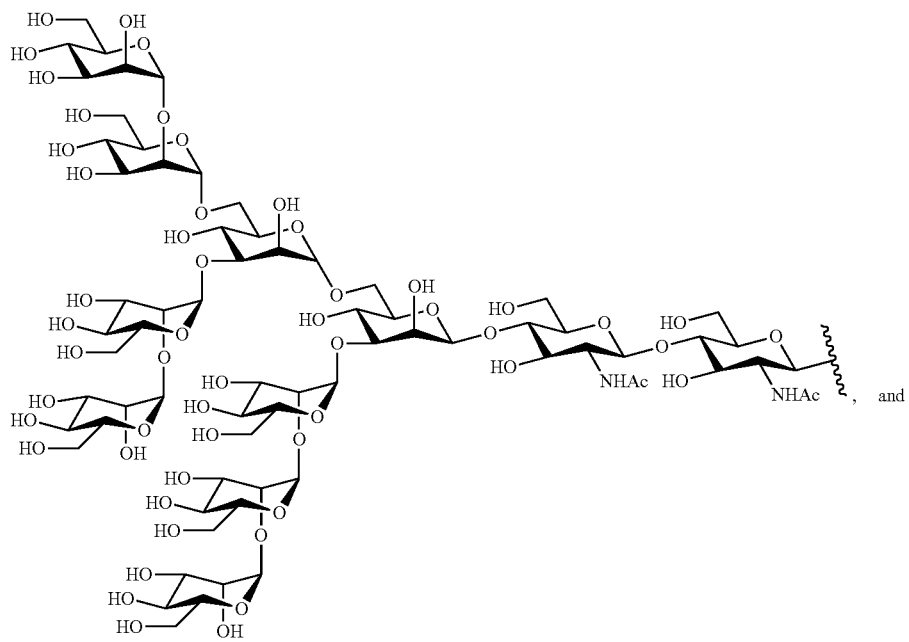

where saccharide subunits include N-acetylglucosamine and mannose as shown (Walther et al., *PLOS Pathogens* 9(3): e1003223 (2013), which is hereby incorporated by reference in its entirety).

Exemplary N-linked glycan structures recognized by HIV broadly neutralizing antibodies (PGT151-PGT158) include multi-antennary complex-type N-glycans with terminal galactose with and without sialic acid residues:

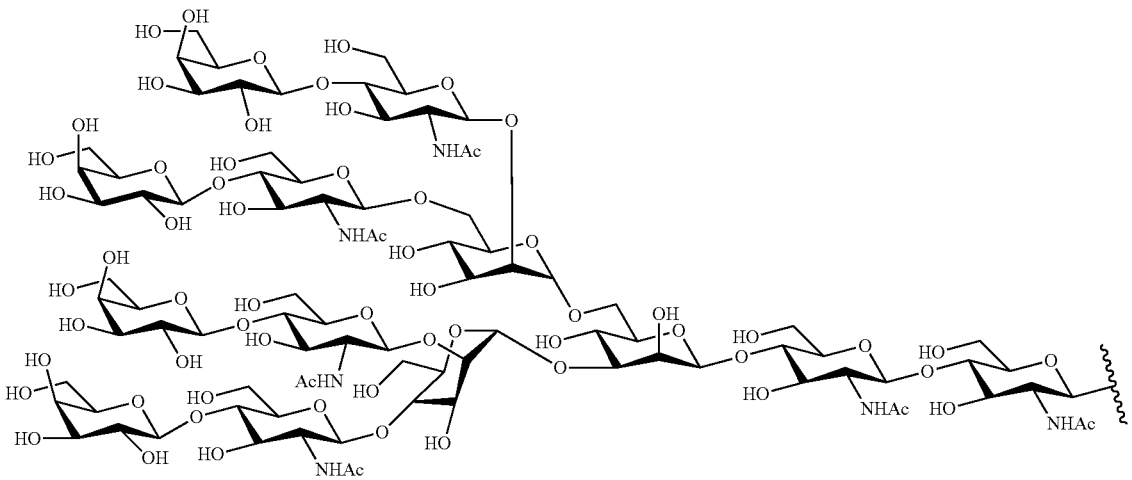,
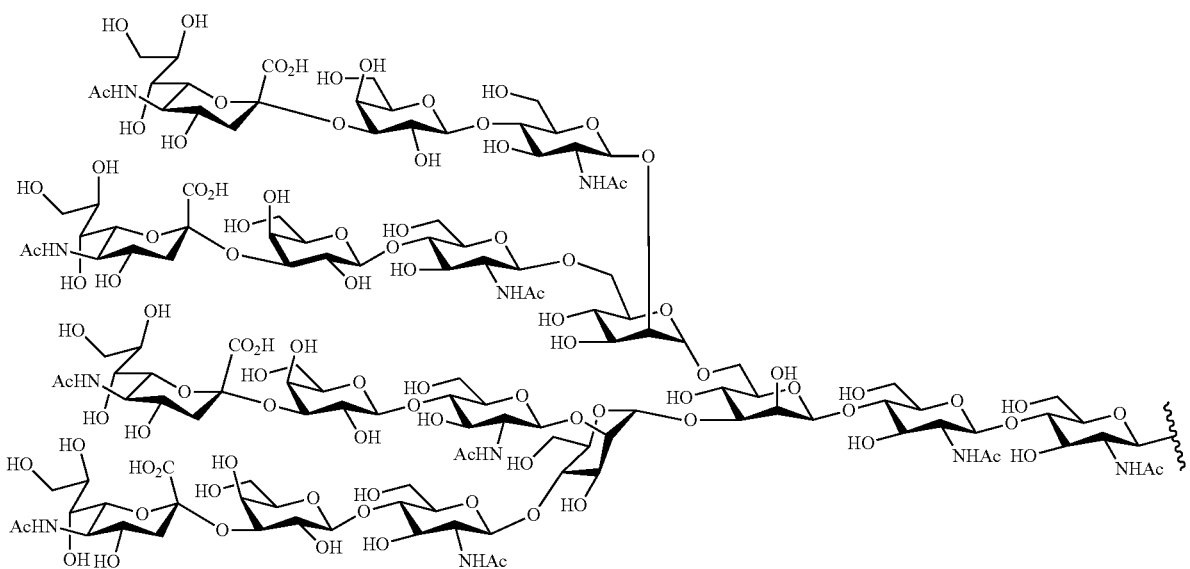,
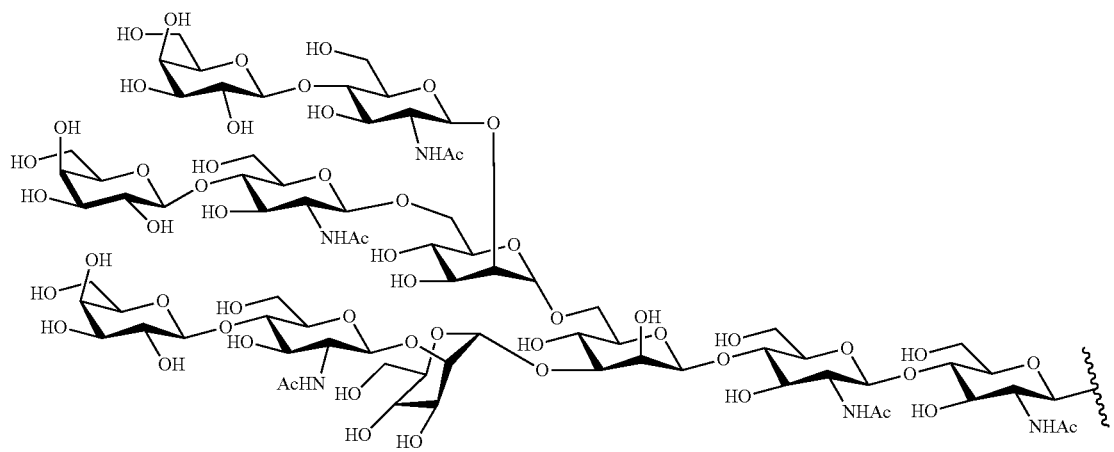

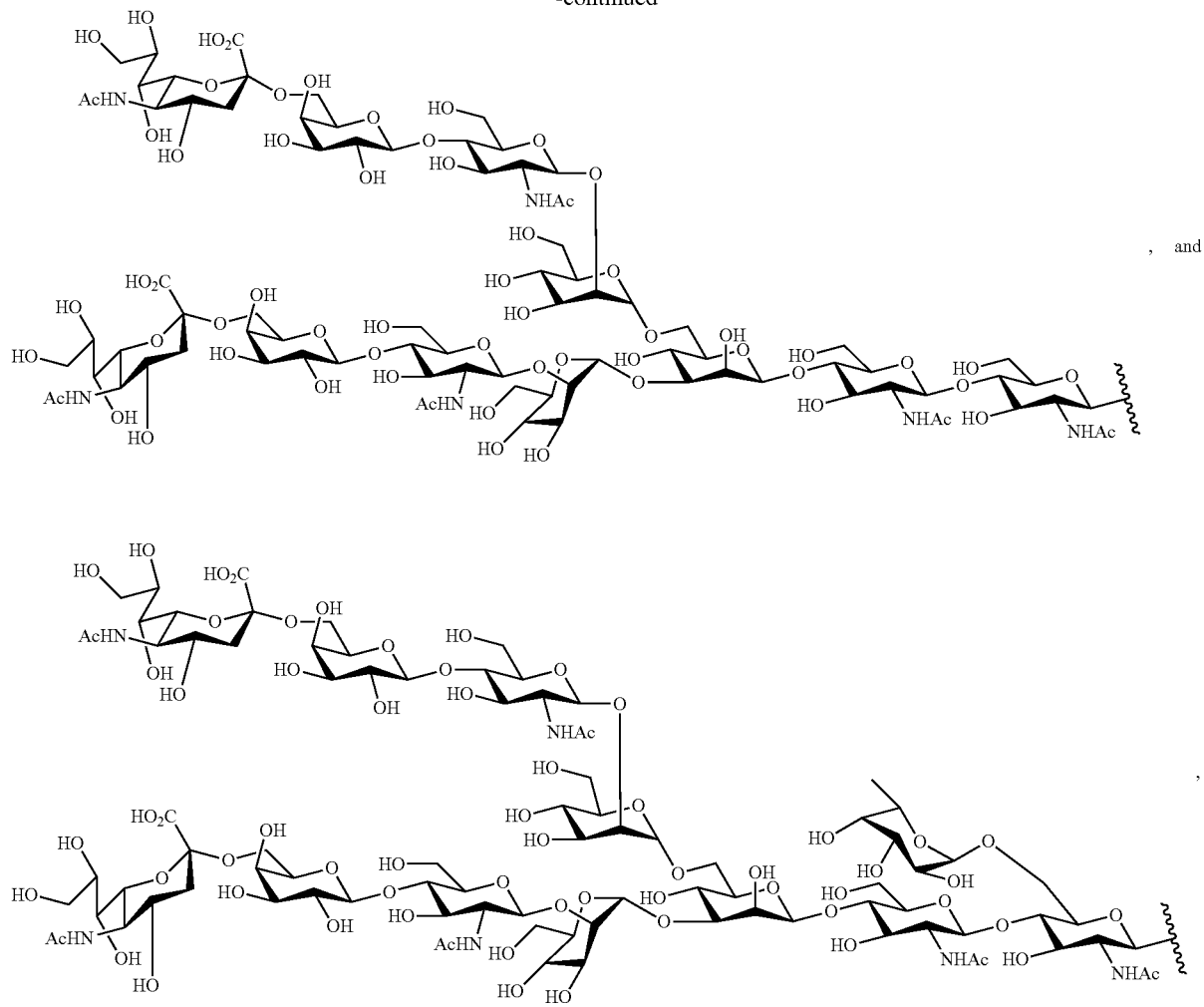
where saccharide subunits include N-acetylglucosamine, mannose, galactose, sialic acid, and fucose as shown (Walther et al., *PLOS Pathogens* 9(3):e1003223 (2013) and Falkowska et al., *Immunity* 40(5): 657-6688 (2014), which are hereby incorporated by reference in their entirety).
Additional exemplary N-linked glycan structures include hybrid-type glycans recognized by HIV antibody PG16:
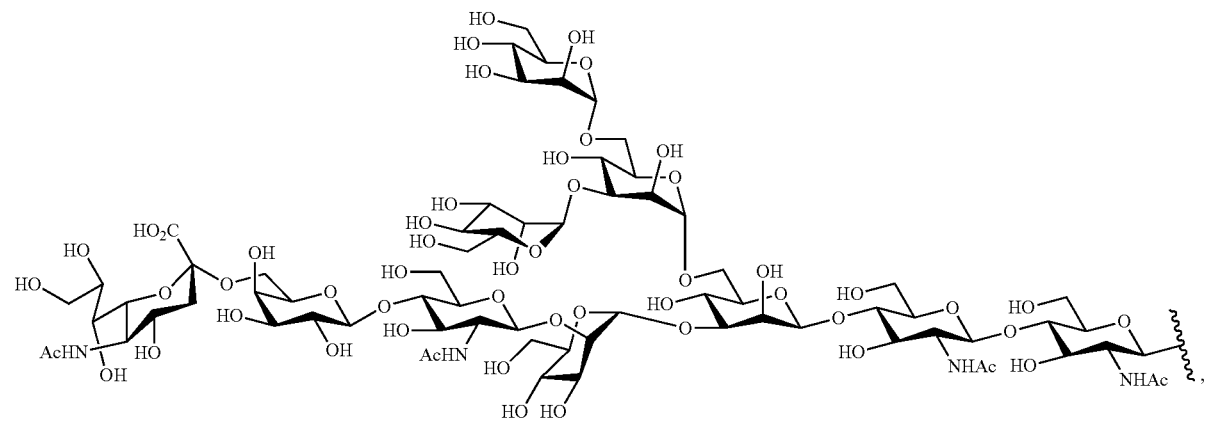

where saccharide subunits include N-acetylglucosamine, mannose, galactose, and sialic acid (Pancera et al., *Nature Struct Mol Biol.* 20(7): 804-13 (2013), which is hereby incorporated by reference in its entirety).

Derivatization of the monosaccharides and/or oligosaccharides to introduce the reactive azido, alkynyl, alkenyl, or thiol group can be achieved using known procedures. See, e.g., Hoyle et al., *Angew. Chem. Int. Ed.* 49:1540-1573 (2010); Temme et al., *Chem. Eur. J.* 19:17291-17295 (2013); Hong et al., *Angew. Chem. Int. Ed.* 48:9879-9883 (2009); MacPherson et al., *Angew. Chem. Int. Ed.* 50:11238-11242 (2011); Kolb et al., *Angew. Chem. Int. Ed.* 40:2004-2021 (2001); Rostovtsev et al., *Angew. Chem. Int. Ed.* 41:2596-2599 (2002); Gierlich et al., *Org. Lett.* 8:3639-3642 (2006); Gierlich et al., *Chem. Eur. J.* 13:9486-9494 (2007), each of which is hereby incorporated by reference in its entirety).

Additional exemplary modified oligosaccharides (suitable for click reaction) include the following:

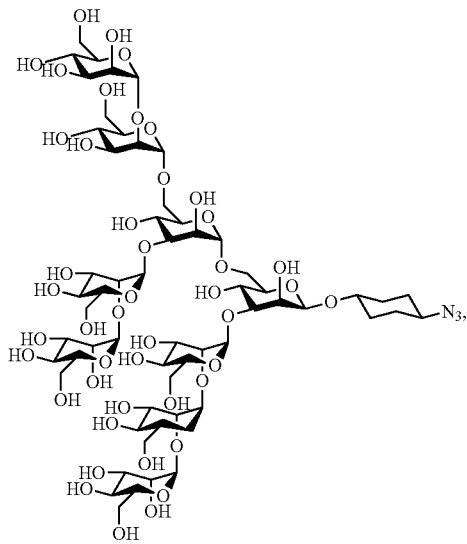

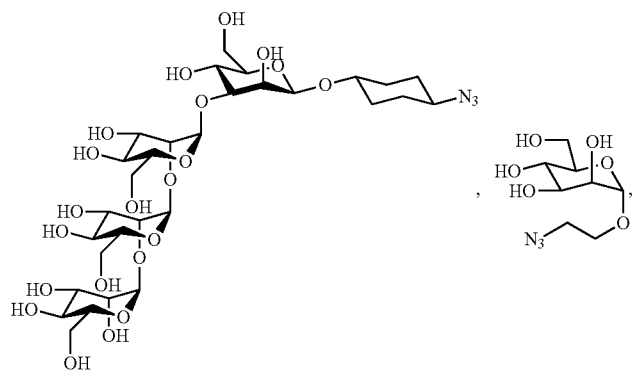

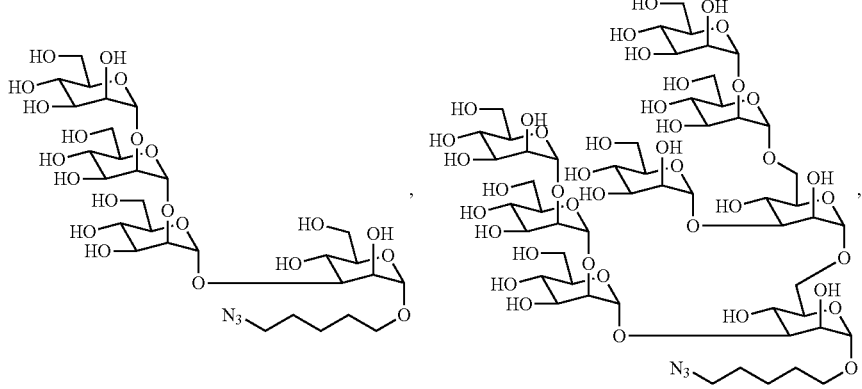

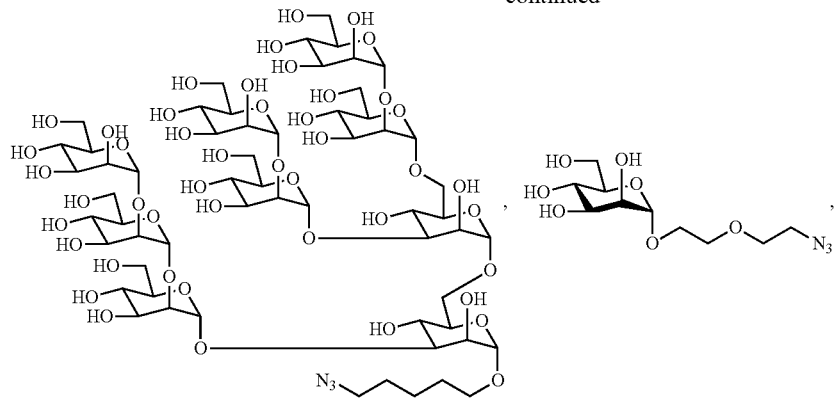
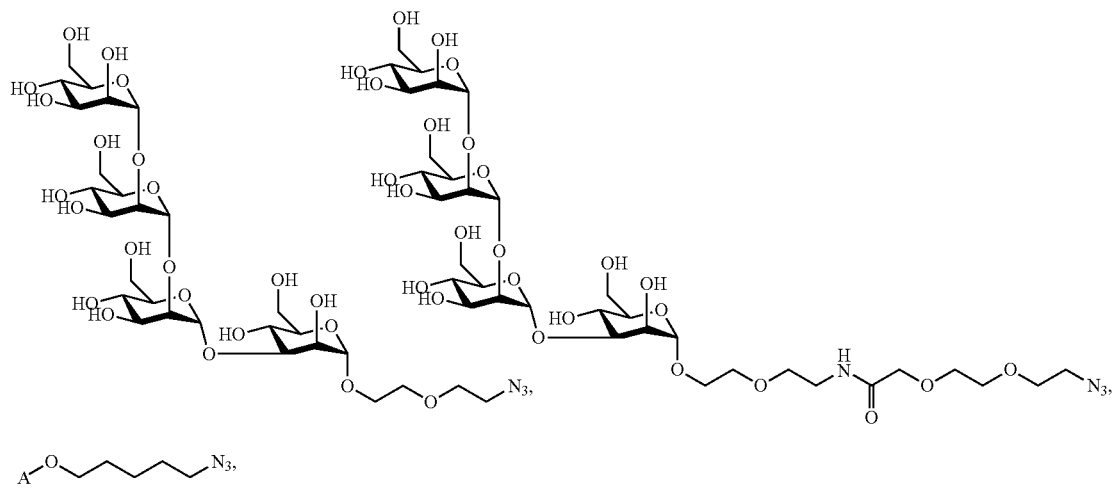
where A is the mono- or oligosaccharide,
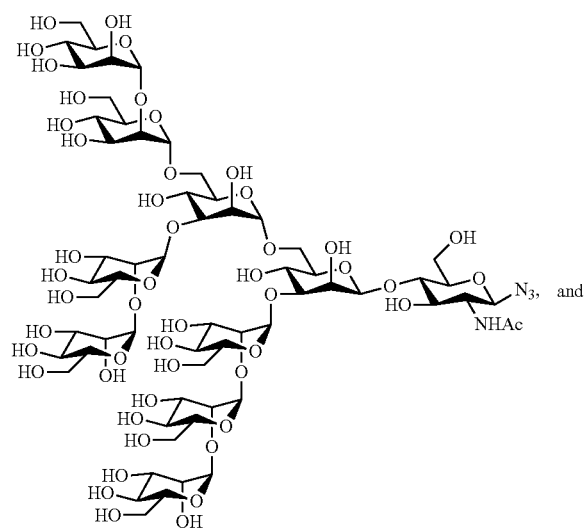
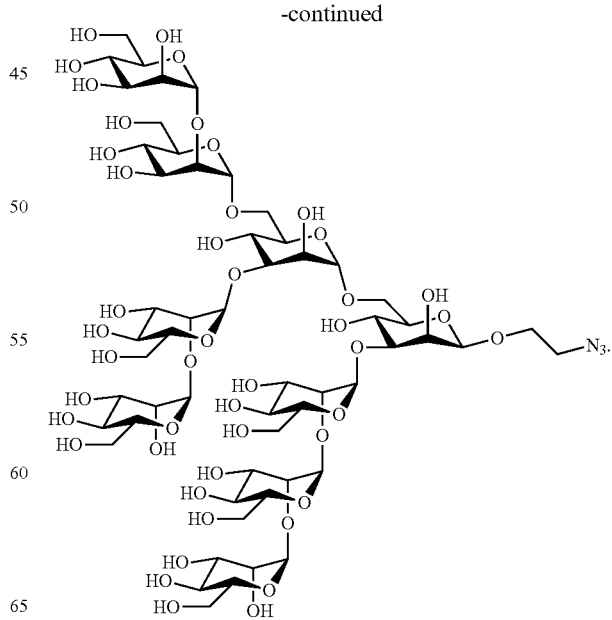

As an alternative to the above structures bearing an azide functional group, equivalent structures can be created with alkynyl, alkenyl, or thiol functional groups.

Tumor-associated carbohydrates ("TACAs") can be linked to lipids such as gangliosides, or to proteins such as mucins. Exemplary glycolipid TACAs includes GM2, GD2, GD3, fucosyl-GM1, Globo-H, and Lewis$^y$ (Le$^y$) and the glycoprotein TACAs include the truncated Tn-, TF and sialylated Tn (STn)-antigens as well as Globo-H and Le$^y$ (Buscas et al., *Chem Commun* (*Camb*). (36): 5335-49 (2009), which is hereby incorporated by reference in its entirety):

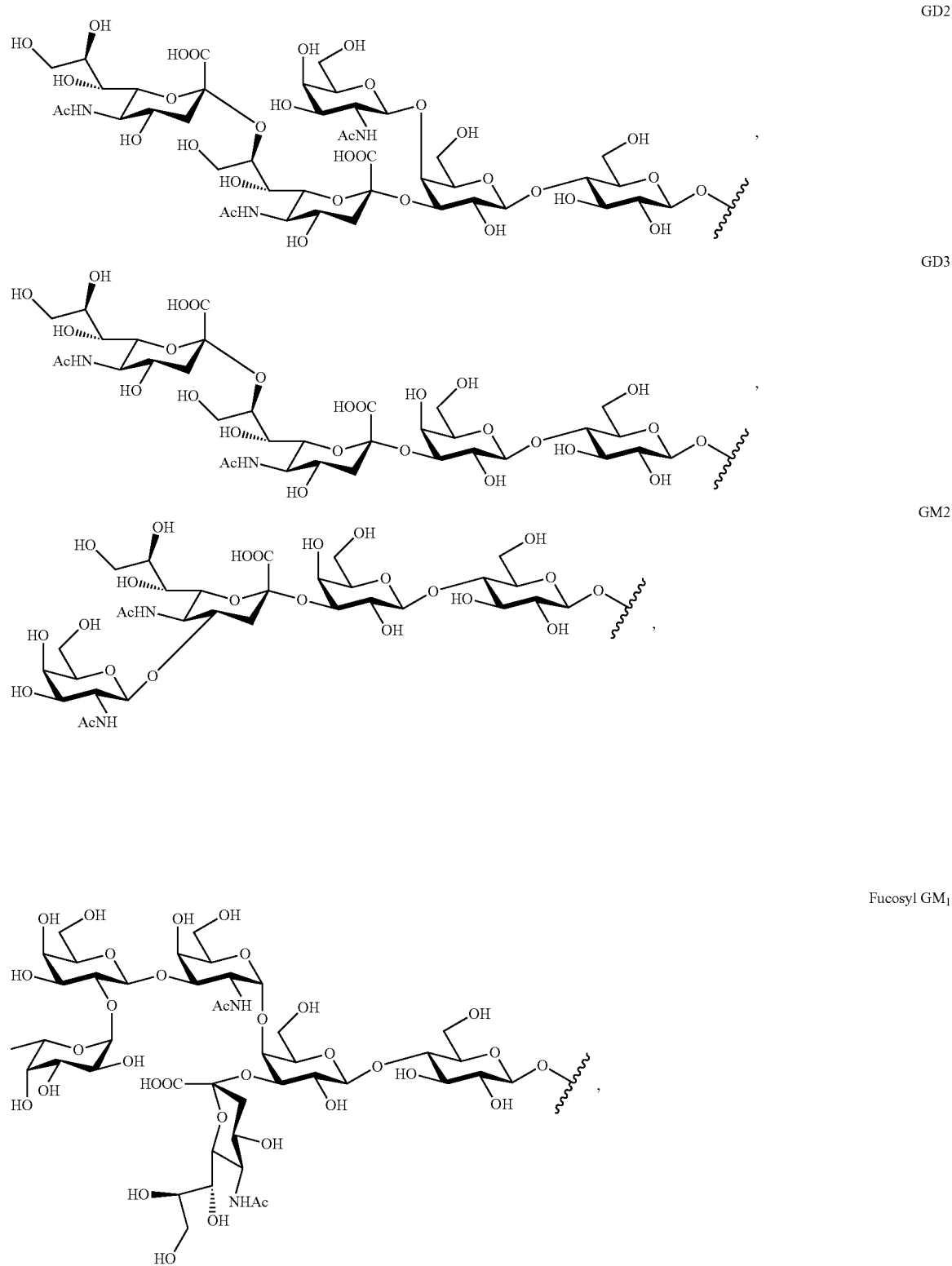

-continued
Globo-H
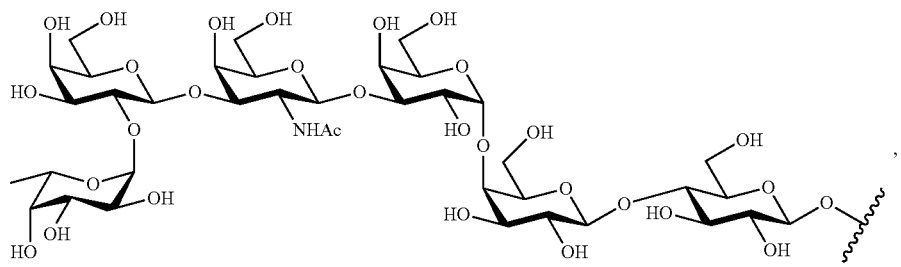
Le<sup>y</sup>
SLe<sup>x</sup>
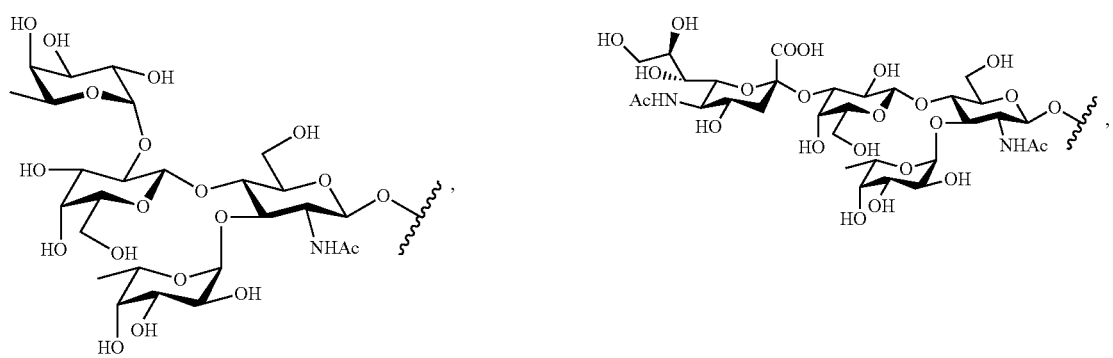
SLe<sup>a</sup>
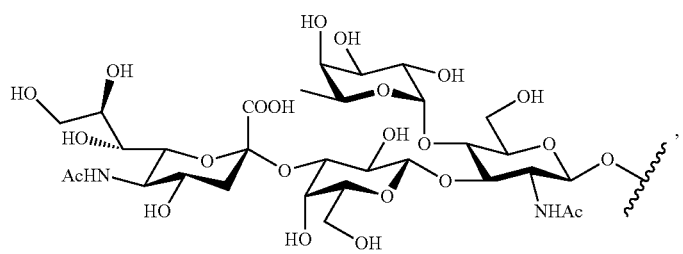
KH-1
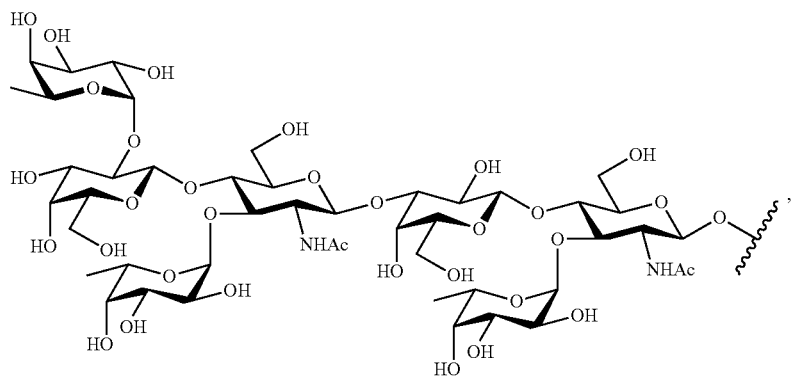

-continued

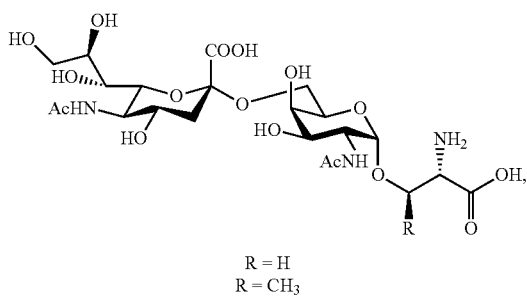
STn
R = H
R = CH₃

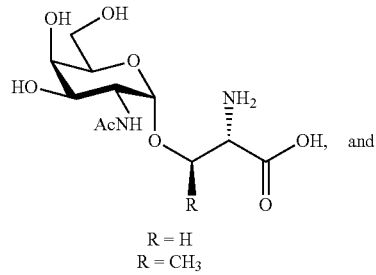
Tn
R = H
R = CH₃

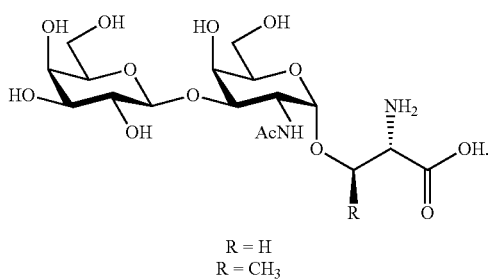
TF
R = H
R = CH₃

These structures can be derivatized to include an azido, alkynyl, alkenyl, or thiol group using the procedures identified above.

An exemplary GPI glycan includes the synthetic non-toxic malarial GPI glycan structure NH₂—CH₂—CH₂—PO₄-(Manα1-2)6Manα1-2Mana-6Manα1-4GlcNH₂α1-6myo-inositol-1,2-cyclic-phosphate (Schofield et al., *Nature* 418(6899):785-9 (2002), which is hereby incorporated by reference in its entirety):

This structure can be derivatized to include an azido, alkynyl, alkenyl, or thiol group using the procedures identified above.

As a result of the click reaction between the modified nucleoside and the modified monosaccharide or oligosaccharide, the modified nucleoside contains a linker molecule between the nucleoside base and the monosaccharide or oligosaccharide. Exemplary linker molecules include, without limitation:

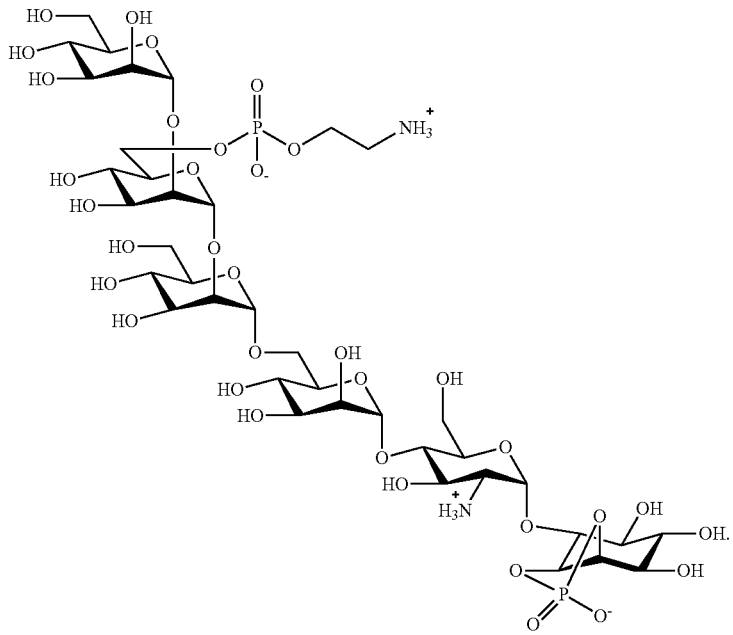

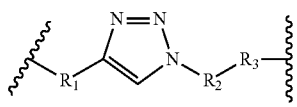

(resulting from the azide-alkyne reaction) or

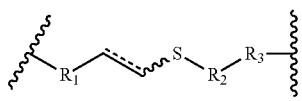

(resulting from the alkene/alkyne-thiol reaction), wherein each of $R_1$ and $R_2$ is optionally a direct link or independently selected from the group consisting of a linear or branched $C_1$ to $C_{18}$ hydrocarbon that is saturated or mono- or poly-unsaturated, optionally interrupted by one or more non-adjacent —O—, —C(=O)—, or —NR$_4$—; a substituted or unsubstituted $C_3$ to $C_{10}$ cycloalkandiyl, a substituted or unsubstituted aryl diradical; a substituted or unsubstituted heteroaryl diradical; a monosaccharide diradical; or a disaccharide diradical; $R_3$ is optional and can be —O—, —S—, or —NR$_4$—; and $R_4$ is H or a $C_1$ to $C_{10}$ alkyl.

Although flexible linkers may be used, the linker between the monosaccharide/oligosaccharide and the modified amino acid(s) of the glycopeptide preferably includes one or more cyclic moieties which offer some rigidity to the resulting glycosyl group.

Once the stem-loop structure is decorated with the one or more monosaccharides or oligosaccharides, a primer is introduced for hybridization to a complementary region of the loop structure, and a primer extension reaction is carried out using dNTPs and a polymerase having strand displacement activity (see Binley et al., *J. Virol.* 78:13232-13252 (2004), which is hereby incorporated by reference in its entirety). This primer extension results in the formation of modified, single-strand-double-strand hybrid oligonucleotides that are glycosylated within the single-strand region. Collectively, these structures constitute the first pool available for selection against a target molecule.

Exemplary target molecules suitable for selection include those that bind to glycosylated naturally occurring proteins, such as monoclonal antibodies that bind to glycosylated epitopes (i.e., carbohydrate-binding monoclonal antibodies). Suitable carbohydrate-binding monoclonal antibodies include those that are neutralizing against a pathogen, as well as those that are cytotoxic against a cancer cell.

Exemplary carbohydrate-binding neutralizing monoclonal antibodies include those that bind specifically to N-glycosylated HIV gp120, N-glycosylated HIV gp41, a combination of N-glycosylated HIV gp120 and gp41, or N-glycosylated HSV-2 gD. Specific examples of these neutralizing monoclonal antibodies include, without limitation, 2G12, PG9, PG16, PGT121, PGT122, PGT123, PGT125, PGT126, PGT127, PGT128, PGT129, PGT130, PGT131, PGT135, PGT136, PGT137, PGT141, PGT142, PGT143, PGT144, PGT145, PGT151, PGT152, PGT153, PGT154, PGT155, PGT156, PGT157, PGT158, CH01, CH02, CH03, CH04, 10-1074, 10-996, 10-1146, 10-847, 10-1341, 10-1121, 10-1130, 10-410, 10-303, 10-259, 10-1369, and E317.

Exemplary carbohydrate-binding cytotoxic monoclonal antibodies include those that binds specifically to O-glycosylated cancer-specific human podoplanin; aberrantly O-glycosylated cancer-specific MUC1, aberrantly O-glycosylated cancer-specific Integrin α3β1, or N-glycosylated cancer-specific antigen RAAG12. Specific examples of these cytotoxic monoclonal antibodies include, without limitation, LpMab-2 (Kato et al., *Sci Rep.* 4:5924 (2014), which is hereby incorporated by reference in its entirety), 237 MAb (Brooks et al., *PNAS* 107(22):10056-10061 (2010), which is hereby incorporated by reference in its entirety), RAV12 (Loo et al., Mol. Cancer Ther. 6(3):856-65 (2007), which is hereby incorporated by reference in its entirety), BCMab1 (*Clinical Cancer Research* 20(15):4001 (2014), which is hereby incorporated by reference in its entirety), DF3 and 115D8 (Tang et al., *Clin Vaccine Immunol.* 17(12): 1903-1908 (2010), which is hereby incorporated by reference in its entirety), huHMFG1, HT186-B7, -D11 and -G2 sc-FVs (Thie et al., *PLoS One* 6(1): e15921 (2011), which is hereby incorporated by reference in its entirety), and GOD3-2C4 (Welinder et al. Glycobiol. 21(8):1097-107 (2011), which is hereby incorporated by reference in its entirety).

Selection of library members that bind to the target protein—in the case of the monoclonal antibodies, mimicking the native glycosyl-epitope to which the antibody binds—is carried out in liquid medium. Briefly, the library is introduced into the selection medium with the target protein, incubating the mixture at a temperature above 20° C. for a period of time. In one embodiment, the incubating is carried out at a temperature of greater than 22° C., greater than 23° C., greater than 24° C., greater than 25° C., greater than 26° C., greater than 27° C., greater than 28° C., greater than 29° C., or greater than 29° C. Preferably, the temperature is from about 32° C. to about 42° C. As a possible extension to the scope of the current work, it is possible for the target protein to be immobilized onto a solid support (e.g., protein A, gold nanoparticles, streptavidin beads/surfaces) prior to selection of the library members. Additionally, one could choose to forgo the use of solid capture and perform the selection/affinity capture/library enrichment using another separation technique such as CE or gel shift.

Suitable incubation periods extend from about 5 or 10 minutes up to about 120 minutes, for example about 20 min, about 30 min, about 40 min, about 50 min, about 60 min, about 70 min, about 80 min, about 90 min, about 100 min, or about 110 min.

If the target protein is biotinylated, streptavidin-labeled magnetic beads can be used to recover library members that bind to the target protein. Alternatively, where the target protein is a monoclonal antibody, Protein A or Protein G-labeled magnetic beads can be used to recover library members that bind to the target monoclonal antibody. Regardless of the type of beads used, the beads can be magnetically isolated and washed with selection buffer. To elute the selected library members, the beads can be resuspended in selection buffer and then heated to disrupt the affinity binding between library member and target. Recovered supernatant contains the eluted library members.

Following recovery of the selected library members, the recovered library members are amplified. PCR using Vent (EXO) (NEB) or Phusion HS (Thermo) is performed using forward and reverse primers, and the amplified DNAs can be purified and used to regenerate the next selection round. In certain embodiments, error prone PCR can be used to facilitate evolution of the library. Regardless of the type of PCR performed, primers are used to copy the double-stranded region of the selected, modified, single-strand-double-strand hybrid oligonucleotides that are glycosylated within the single-strand region.

In regenerating the next selection round, the steps of forming the stem-loop oligonucleotides containing one or more modified nucleoside bases; reacting a modified oligosaccharide with the one or more modified nucleoside bases to form glycosylated stem-loop oligonucleotides; and synthesizing a complementary strand (using the glycosylated stem-loop oligonucleotides as templates, the primer that hybridizes to a portion of the loop, dNTPs, and the polymerase having strand displacement activity to form the second pool of modified, single-strand-double-strand hybrid oligonucleotides that are glycosylated within the single-strand region) can be repeated.

Differences in the selection protocol can performed in subsequent rounds. For instance, the selection stringency can be increased to promote the selection of high affinity binding of pool members. In certain embodiments the temperature can be varied from about 20 to 25° C. in early rounds to temperatures greater than 27° C. or even greater than 30° C. (e.g., about 32° C. to about 50° C.) in later rounds. Any such variation in temperature can be used. In alternative embodiments the target protein concentration can be varied from about 25 to about 200 nM in early rounds, and reduced to about 10 to about 80 nM, or about 5 to about 25 nM in later rounds. Any such variation in target protein concentration can be used. In certain embodiments the duration of the selection step can also be reduced from about 20 to about 120 minutes in early rounds, to about 5 to about 20 minutes in later rounds. Any such variation in duration of the selection step can be used. In another embodiment, the introduction of competitor molecules for negative selection can be introduced in later rounds, including the introduction of free monosaccharides or oligosaccharides, the introduction of unglycosylated oligonucleotides (removing oligonucleotides which bind to target protein without being glycosylated), the introduction of unmodified magnetic beads, e.g., streptavidin, Protein A, or Protein G-conjugated beads (removing oligonucleotides or glycosylated oligonucleotides hat bind directly to a solid support), or combinations thereof. Any number of negative selection steps can be employed. In yet another embodiment, the number and conditions of the wash steps can be made more stringent during later selection rounds.

In between rounds or after the final round, the individual, selected pool members can be sequenced and, thus, the oligonucleotide sequence(s) identified.

In one particular embodiment, the modified SELMA method includes the steps of (a) combining a plurality of oligonucleotides, a first DNA polymerase, and a plurality of deoxyribonucleotide triphosphates, where the oligonucleotides comprise a first primer binding site on the 5' end, a randomized region, and a stem-loop region where the randomized region is located between the first primer binding site and the stem-loop region, and the stem-loop region comprises a second primer binding site, and at least one of the deoxyribonucleotide triphosphates comprises a reactive substituent, thereby forming a plurality of extended oligonucleotides comprising an original strand and an extended strand, wherein the extended strand comprises at least one reactive substituent;

(b) combining a plurality of modifying compounds and the plurality of extended oligonucleotides under reaction conditions, thereby forming a plurality of modified extended oligonucleotides comprising the original strand and a modified extended strand;

(c) combining a plurality of primers complementary to the second primer binding site, a second DNA polymerase, the plurality of modified extended oligonucleotides, and a plurality of deoxyribonucleotide triphosphates, thereby creating duplexes with the original strands, displacing the modified extended strands, and forming a plurality of modified single-stranded oligonucleotides;

(d) combining the plurality of modified single-stranded oligonucleotides and a target protein, thereby forming a mixture;

(e) incubating the mixture at a first temperature for a first period of time, wherein the first temperature is from about 32° C. to about 42° C., and the first period of time is from about 30 min to about 2 h;

(f) isolating from the mixture the modified single-stranded oligonucleotides that bind to the target protein, thereby identifying a plurality of selected oligonucleotides;

(g) amplifying the plurality of selected oligonucleotides, thereby forming a plurality of complementary oligonucleotides; and (h) preparing a plurality of regenerated selected oligonucleotides from the plurality of complementary oligonucleotides.

In a preferred embodiment, no thymidine triphosphate is used in step (a).

Regardless of the particular method employed, having selected and identified the glycosylated oligonucleotide sequence that binds specifically to the target molecule, individual glycosylated oligonucleotides can be synthesized such that the molecule primer binding sites or any other functional regions included solely for the SELMA process are omitted. In addition, these oligonucleotides can be prepared with modified or unmodified DNA, modified or unmodified RNA, mixed RNA-DNA, or having PNA backbones. For example, one or more phosphorothioate-linked nucleotides, inverted bases (A, C, G, and T/U) that afford a 3'-3' or 5'-5' reversed linkage, or 2'-fluoro-, 2'-amino, 2'-O-methyl-, 5'-iodo-, or 5'-bromo-modified nucleotides can be used. Other modifications known in the art are also contemplated, particularly those that may influence the in vivo stability of the oligonucleotide. The length of the individual oligonucleotides can be about the same length as the randomized region, as identified above.

Thus, the oligonucleotides of the invention include one or more modified nucleoside bases having the structure:

-B-L-A wherein for each of the modified nucleosides A is independently a monosaccharide or oligosaccharide of the type described above, L is a linker molecule as described above (i.e., product of the click reaction between the reactive mono- or oligosaccharide and the reactive nucleoside), and B is independently a pyrimidine or pyridine base linked to the sugar-phosphate backbone (or alternative backbone as described above) of the oligonucleotide. These oligonucleotides bind specifically to a carbohydrate-binding monoclonal antibody with an affinity of less than 100 nM.

Suitable monosaccharides and oligosaccharides, as well as linker molecules include those described herein-above. Depending on the modified nucleoside used to prepare the oligonucleotide, the pyrimidine or pyridine base, B, can be one or more of (where the bond between the sugar and base is shown using the wedge bond):

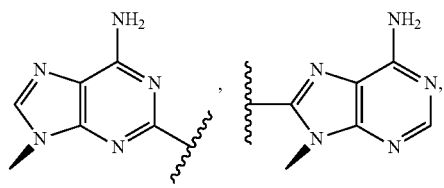

-continued
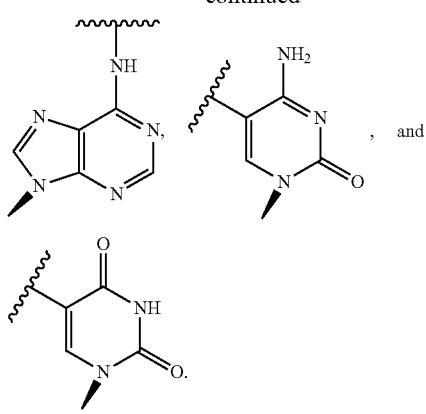

, and 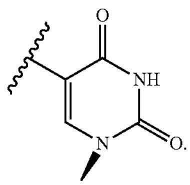 bind specifically to carbohydrate-binding monoclonal antibodies can be prepared and it is expected that, in many instances, these will display higher affinity for the monoclonal antibody than the monoclonal antibody has for its native binding partner.

In certain embodiments, the carbohydrate-binding, neutralizing monoclonal antibody is 2G12, and the oligonucleotide binds specifically to 2G12 with a $K_d$ value that is lower than 20 nM, has a predicted structure, at 37° C., having exactly one stem-loop whereby the loop comprises the nucleotide sequence of AACCNACGGANAAA (SEQ ID NO: 1), where N is one of the modified nucleoside bases (as defined above), and the stem includes at least 3 nucleotide base-pairs and one of the nucleotides in the stem includes a modified nucleoside base (as defined above). Exemplary oligonucleotides sharing these properties include, without limitation, those listed in Table 1 below (see also FIG. 3):

TABLE 1

Sequences of Structural Variants of 2G12-Binding Aptamers

| Name | Sequence | SEQ ID NO: |
|---|---|---|
| E1 | AGACCCACGGNGCAACCNACGGANAAAGCACCG | 2 |
| E1 $_{(nt\ 8-33)}$ | CGGNGCAACCNACGGANAAAGCACCG | 3 |
| E2 | AGACCCTCGGNGCAACCNACGGANAAAGCACCGAGG | 4 |
| E2 $_{(nt\ 5-36)}$ | CCTCGGNGCAACCNACGGANAAAGCACCGAGG | 5 |
| E3 | TGTCCCTCGGNGCAACCNACGGANAAAGCACCGAGGGACA | 6 |

In one embodiment, the oligonucleotide comprises from 2 to about 10 of said modified nucleoside bases. In certain embodiments, the oligonucleotide may contain from 2 to 5 or 2 to 4 of the modified nucleoside bases, and preferably two or more of the modified nucleoside bases are at non-adjacent positions in the oligonucleotide. In certain embodiments, two modified nucleoside bases may be at adjacent positions in the oligonucleotide.

In certain embodiments, A is independently a branched or unbranched oligosaccharide of at least about 3 saccharide moieties up to about 20 saccharide moieties. In one such embodiment, the oligosaccharide consists of 9 saccharide moieties, one example of which is a branched oligosaccharide containing exactly 9 mannose moieties.

In certain embodiments, the oligonucleotide binds specifically to the carbohydrate-binding monoclonal antibody with an affinity ($K_d$) of less than 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM.

In certain embodiments, the oligonucleotide binds specifically to the carbohydrate-binding monoclonal antibody with an affinity that is substantially the same as or lower than the affinity of the carbohydrate-binding monoclonal antibody to its naturally occurring binding partner. As used herein, an affinity that is "substantially the same" means that a Kd of the oligonucleotide for its target monoclonal antibody is less than 5×, less than 4×, less than 3×, less than 2×, or less than 1.5× Kd of the native binding partner to the monoclonal antibody. In certain embodiments, the oligonucleotide binds specifically to the carbohydrate-binding monoclonal antibody with an affinity that is lower than the affinity of the carbohydrate-binding monoclonal antibody to its naturally occurring binding partner.

Exemplary neutralizing monoclonal antibodies and cytotoxic monoclonal antibodies are identified above. Using the selection protocol described herein, oligonucleotides that In certain embodiments, the oligonucleotides identified in the preceding paragraph are characterized by binding to HIV neutralizing monoclonal antibody 2G12 with a $K_d$ value that is lower than 10 nM and $Fb_{max}$ value (in percent) that is greater than about 60, more preferably greater than 62, 64, 66, 68, or 70.

In certain embodiments, the oligonucleotides identified in the preceding paragraphs are oligodeoxynucleotides and the modified nucleoside bases comprises the structure according to formula (IV), with the deoxyribose sugar being shown:

(IV)

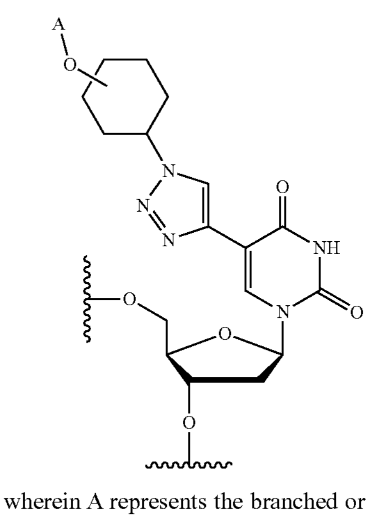

wherein A represents the branched or unbranched oligosaccharide. In one preferred embodiment of formula (IV), A represents a branched or unbranched oligosaccharide consisting of 9 saccharide moieties. In another preferred embodiment, A represents a branched oligosaccharide consisting of 9 mannose moieties.

A further aspect of the invention relates to an immunogenic conjugate that includes an oligonucleotide of the invention covalently or non-covalently bound to an immunogenic carrier molecule. Exemplary immunogenic carrier molecule include, without limitation, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

Any of a variety of conjugation methodologies can be utilized. See, e.g., Jennings et al., *J. Immunol.* 127:1011-8 (1981); Beuvery et al., *Infect. Immun* 40:39-45 (1993), each of which is hereby incorporated by reference in its entirety. In one approach terminal aldehyde-modified DNA groups can be cross-linked through reductive amination with free amino groups on the protein, mostly lysines. In another approach, a carbodiimide-mediated reaction is performed to cause amide bond formation through the use of functional groups from a carrier and carboxyl modified oligonucleotide. Finally, NHS ester-maleimide heterobifunctional crosslinker can be used by activating the carrier protein with SMCC to create an intermediate maleimide derivative, which is then coupled to thiol-modified oligonucleotide to form thioether bonds.

A further aspect of the invention relates to a pharmaceutical composition that includes a pharmaceutically acceptable carrier and an oligonucleotide or immunogenic conjugate of the invention.

Pharmaceutical compositions suitable for injectable or parental use (e.g., intravenous, intra-arterial, intramuscular, etc.) or intranasal use may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water, saline solutions, and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

The pharmaceutical compositions of the present invention may also be administered directly to the airways in the form of an aerosol. For use as aerosols, the compositions of the present invention in the form of a solution or suspension may be packaged in a pressurized aerosol container together with suitable propellants, for example, hydrocarbon propellants like propane, butane, or isobutane with conventional adjuvants. The pharmaceutical compositions of the present invention also may be administered in a non-pressurized form such as in a nebulizer or atomizer. Formulations suitable for intranasal nebulization or bronchial aerosolization delivery are also known and can be used in the present invention (see Lu & Hickey, "Pulmonary Vaccine Delivery," *Exp Rev Vaccines* 6(2):213-226 (2007) and Alpar et al., "Biodegradable Mucoadhesive Particulates for Nasal and Pulmonary Antigen and DNA Delivery," *Adv Drug Deliv Rev* 57(3):411-30 (2005), which are hereby incorporated by reference in their entirety.

The pharmaceutical compositions of the present invention can also include an effective amount of a separate adjuvant. Suitable adjuvants for use in the present invention include, without limitation, aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid, Quil A, non-infective *Bordetella pertussis*, QS-21, monophosphoryl lipid A, an alpha-galactosylceramide derivative, or PamCys-type lipids.

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Advanced Drug Delivery Reviews* 32:173-186 (1998), which is hereby incorporated by reference in its entirety) alone or optionally all combinations thereof are suitable for human administration.

The pharmaceutical compositions can also include one or more additives or preservatives, or both.

Effective amounts of the oligonucleotide may vary depending upon many different factors, including mode of administration, target site, physiological state of the patient, other medications administered, and whether treatment is prophylactic or therapeutic. Treatment dosages need to be titrated to optimize safety and efficacy. The amount of oligonucleotide immunogen depends on whether adjuvant is also administered, with higher dosages being required in the absence of adjuvant. The amount of an oligonucleotide immunogen for administration sometimes varies from 1 µg-5 mg per patient and more usually from 5-1000 µg per injection for human administration.

The oligonucleotides, immunogenic conjugates, and pharmaceutical compositions can be incorporated into a delivery vehicle to facilitate administration. Such delivery vehicles include, but are not limited to, biodegradable microspheres (MARK E. KEEGAN & W. MARK SALTZMAN, *Surface Modified Biodegradable Microspheres for DNA Vaccine Delivery, in* DNA VACCINES: METHODS AND PROTOCOLS 107-113 (W. Mark Saltzman et al., eds., 2006), which is hereby incorporated by reference in its entirety), microparticles (Singh et al., "Nanoparticles and Microparticles as Vaccine Delivery Systems," *Expert Rev Vaccine* 6(5):797-808 (2007), which is hereby incorporated by reference in its entirety), nanoparticles (Wendorf et al., "A Practical Approach to the Use of Nanoparticles for Vaccine Delivery," *J Pharmaceutical Sciences* 95(12):2738-50 (2006) which is hereby incorporated by reference in its entirety), liposomes (U.S. Patent Application Publication No. 2007/0082043 to Dov et al. and Hayashi et al., "A Novel Vaccine Delivery System Using Immunopotentiating Fusogenic Liposomes," *Biochem Biophys Res Comm* 261(3): 824-28 (1999), which are hereby incorporated by reference in their entirety), collagen minipellets (Lofthouse et al., "The Application of Biodegradable Collagen Minipellets as Vaccine Delivery Vehicles in Mice and Sheep," *Vaccine* 19(30):4318-27 (2001), which is hereby incorporated by reference in its entirety), and cochleates (Gould-Fogerite et al., "Targeting Immune Response Induction with Cochleate and Liposome-Based Vaccines," *Adv Drug Deliv Rev* 32(3):273-87 (1998), which is hereby incorporated by reference in its entirety).

The oligonucleotides, immunogenic conjugates, and pharmaceutical compositions can be used to induce an immune response in an individual. The individual can be any mammal, particularly a human, although veterinary usage is also contemplated. This method is carried out by administering one of these active agents to an individual in a manner that is effective to induce an immune response against the oligonucleotide. Because the oligonucleotide mimics the native glycosylated epitope of a native target of the monoclonal antibody to which the oligonucleotide was selected, certain oligonucleotides can induce a carbohydrate-binding, neutralizing antibody response that is protective against a pathogen (e.g., viral or bacterial pathogen) and certain other oligonucleotides can induce a carbohydrate-binding, cytotoxic antibody response against a cancer cell that expresses a glycosylated antigen.

For each of these embodiments, administration of the oligonucleotides, immunogenic conjugates, and/or pharmaceutical compositions can be carried orally, parenterally, subcutaneously, intravenously, intramuscularly, intraperitoneally, by intranasal instillation, by implantation, by intracavitary or intravesical instillation, intraarterially, intralesionally, transdermally, intra- or peri-tumorally, by application to mucous membranes, or by inhalation. Administration of these agents can be repeated periodically.

Exemplary viruses include, without limitation, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1 or HIV-2), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Acute Respiratory Syndrome (SARS Co-V), Tickborne Encephalitis virus, Varicella zoster virus, Venezuelan Equine Encephalitis virus, Yellow Fever virus, Western Equine Encephalitis virus, and West Nile virus.

Exemplary bacteria include, without limitation, *Bacillus anthracis, Bordetella pertussis B, Borrelia burgdorferi, Chlamydia trachomatis, Clostridium difficile, Clostridium tetani, Candida albicans, Corynebacterium diphtherias, Cryptococcus neoformans, Entamoeba histolytica, Escherichia coli, Francisella tularensis, Haemophilus influenzae* (nontypeable), *Helicobacter pylori, Histoplasma capsulatum, Moraxella catarrhalis, Mycobacterium leprae, Mycobacterium tuberculosis, Neisseria gonorrheae, Neisseria meningitides, Pseudomonas aeruginosa, Staphylococcus aureus*, Methicillin-resistant *Staphylococcus aureus, Streptococcus agalactiae, Streptococcus pneumoniae, Streptococcus pyogenes*, and *Yersinia pestis*.

For prophylactic treatment against viral or bacterial infection, it is intended that the oligonucleotides, immunogenic conjugates, and pharmaceutical compositions of the present invention can be administered prior to exposure of an individual to the virus or bacteria and that the resulting immune response can inhibit or reduce the severity of the viral or bacterial infection such that the virus or bacteria can be eliminated from the individual. The oligonucleotides, immunogenic conjugates, and pharmaceutical compositions of the present invention can also be administered to an individual for therapeutic treatment. In accordance with one embodiment, it is intended that the composition(s) of the present invention can be administered to an individual who is already exposed to the virus or bacteria. The resulting enhanced immune response can reduce the duration or severity of the existing viral or bacterial infection, as well as minimize any harmful consequences of untreated viral or bacterial infections. The composition(s) can also be administered in combination other therapeutic anti-viral or anti-bacterial regimen. In asymptomatic patients, treatment can begin at any age (e.g., 10, 20, 30 years of age). Treatment typically entails multiple dosages over a period of time. Treatment can be monitored by assaying antibody, or activated T-cell or B-cell responses to the therapeutic agent over time. If the response falls, a booster dosage is indicated.

The oligonucleotides, immunogenic conjugates, and pharmaceutical compositions that induce a cytotoxic antibody response against a cancer cell antigen can be used to treat solid tumors and blood cancers (leukemia or lymphoma) that are characterized by expression of O-glycosylated cancer-specific human podoplanin; aberrantly O-glycosylated cancer-specific MUC1, aberrantly O-glycosylated cancer-specific integrin α3β1, or N-glycosylated cancer-specific antigen RAAG12.

Exemplary cancers that display one of the glycosylated cancer-specific antigen include colorectal cancer, gastric cancer, ovarian cancer, breast cancer, and pancreatic cancer, which display N-glycosylated RAAG12; squamous cell carcinoma, lung and esophageal carcinoma, testicular seminoma, malignant brain tumor, fibrosarcoma, malignant mesothelioma, bladder cancers, and testicular cancers that display O-glycosylated ppodoplanin; bladder cancers that display O-glycosylated integrin a3β1; breast cancer, ovarian cancer, lung cancer, pancreatic cancer, prostate cancer, and forms of leukemia that displays aberrantly O-glycosylated MUC1.

For cancer therapy, it is contemplated that the oligonucleotides, immunogenic conjugates, and pharmaceutical compositions can be administered in combination with a chemotherapeutic agent, a radiation therapy, or alternative immunotherapeutic agent. The specific selection of chemotherapeutic agent, a radiation therapy, or alternative immunotherapeutic agent will depend on the type of cancer. These agents can also be administered in combination with surgical resection to remove cancerous tissue, with treatment being carried out before, after, or both before and after surgery.

For inducing the immune response, the amount of an oligonucleotide for administration sometimes varies from 1 µg-5 mg per patient and more usually from 5-1500 µg per dose for human administration. Occasionally, a higher dose of 1-2 mg per injection is used. Typically about 10, 20, 50, or 100 µg is used for each human dose. The mass of oligonucleotide immunogen also depends on the mass ratio of immunogenic epitope within the oligonucleotide immunogen to the mass of oligonucleotide immunogen as a whole. Typically, $10^{-3}$ to $10^{-5}$ micromoles of immunogenic epitope are used for each microgram of oligonucleotide immunogen. The timing of injections can vary significantly from once a day, to once a year, to once a decade. On any given day that a dosage of oligonucleotide immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster administration at time intervals, such as 6 week intervals. Another regimen consists of an immunization followed by booster injections 1, 2, and 12 months later. Another regimen entails an administration every two months for a prolonged period in excess of 12 months. Alternatively, booster injections can be on an irregular basis as indicated by monitoring of immune response.

In certain embodiments, multiple doses are given over a period of time, each using a different immunogenic oligonucleotide in an appropriate amount, as indicated above.

The oligonucleotides of the invention can also be used to detect a neutralizing antibody in a patient sample (e.g., a serum sample). This method includes providing an oligonucleotide of the invention, contacting the oligonucleotide with a sample from an individual; and detecting whether the oligonucleotide binds specifically to an antibody present in the sample, wherein the detection of the antibody is carried out using a label.

Exemplary labels include, without limitation, a radiolabel, fluorescent label, enzymatic label, chemiluminescent marker, biotinyl group, an epitope recognized by a secondary reporter, a magnetic agent, or a toxin.

The detection step is preferably carried using a suitable assay format. Exemplary assays include, without limitation, ELISA, radioimmunoassay, gel-diffusion precipitation reaction assay, immunodiffusion assay, agglutination assay, fluorescent immunoassay, immunoelectrophoresis assay, surface plasmon resonance assay, or biolayer interferometry assay. In certainly of these assay formats, a secondary antibody is used to label the antibody bound specifically to the oligonucleotide. Depending on the type of assay, the oligonucleotide can be in the solution phase or coupled to a solid surface.

EXAMPLES

The examples below are intended to exemplify the practice of the present invention but are by no means intended to limit the scope thereof.

Materials and Methods

All reagents, buffers and buffer components were purchased from National Diagnostics, Sigma-Aldrich, Acros Organics, New England Biolabs, or Fisher and used without further purification. Nitrocellulose membranes (0.45 μm) were purchased from Biorad. PVDF membranes (0.45 μm, immobilon-FL) were purchased from Millipore. Water was purified with a Milli-Q Ultrapure water purification system. Prepared buffers were sterilized by filtration through 0.22 μm syringe filters obtained from Millipore.

Man$_9$-azide was prepared according to literature (Temme et al., *Chem. Eur. J.* 19:17291-17295 (2013), which is hereby incorporated by reference in its entirety). The chemical structure of Man$_9$-azide is shown in PCT Publ. No. WO 2015/084846, which is hereby incorporated by reference in its entirety.

Preparation of Selected Clones and Mutants for Filter Binding Assay: For binding studies, the template synthetic oligos for each clone were obtained from Integrated DNA Technologies. Each clone (100 pmol) was prepared by polymerase extension of a primer against the synthetic template (using EdUTP in place of dTTP), then glycosylated using vacuum degassing method and purified via urea PAGE (Binley et al., *J. Virol.* 78:13232-13252 (2004), which is hereby incorporated by reference in its entirety). The glycosylated and purified ssDNA was then radioactively phosphorylated using polynucleotide kinase and ATP ($\gamma$-$^{32}$P) according to manufacturer's instructions. The desalted radiolabeled glycosylated aptamer was then used in the filter binding assay described below.

Filter Binding: Binding Buffer (20 mM Tris HCl pH 7.5, 150 mM NaCl, 4 mM MgSO$_4$, 50 ug/mL BSA) was prepared freshly and filtered through 0.2 μM syringe filter.

2G12 serial dilution was prepared in quadruplet. 2G12 dilutions of 500 nM, 125 nM, 31.25 nM, 7.81 nM, 1.95 nM, 0.49 nM, 0.12 nM, and 0.03 nM were used in the filter binding assays.

Sufficient radiolabeled DNA (enough to produce an adequate radiogram after overnight exposure, generally 50-100 fmol) was added to 180 μl binding buffer/BSA. The solution was heated to 70° C. for 5 minutes and allowed to cool to room temperature. Then, 5 μL of the radiolabeled and diluted aptamer was added to a 50 μL aliquot of the antibody. For each dilution, the experiment was repeated in quadruplicate. After binding for 1 hr, the solution was then filtered through a nitrocellulose/PVDF sandwich and the radioactivity in each membrane quantified by exposure to a phosphor screen followed by phosphor imaging. The data were then fit to the equation $F_{bound}=(F_{max}[2G12])/(K_d[2G12])$.

Nitrocellulose was exposed to 0.4 M NaOH for 10 minutes, washed extensively with H$_2$O, and then soaked in binding buffer prior to the filter binding assay. PVDF was soaked in methanol prior to extensive washing with H$_2$O and soaking in binding buffer prior to the filter binding assay.

Example 1—Modification of 2G12 Binding Aptamers

As reported in PCT Publ. No. WO 2015/084846, which is hereby incorporated by reference in its entirety, clones 1 (SEQ ID NO: 7) and 2 (SEQ ID NO: 15) possess the following sequences and 2G12 binding properties.

TABLE 2

Sequences, Multivalency and 2G12 Binding of Clones from 37° C. Man$_9$ Selection

| Clone | Glycans | Sequence[a] | $K_d$ (nM)[b] | Fb$_{max}$[b] |
|---|---|---|---|---|
| 1 | 3 | AGACCCACGGSGCAACCSACGGASA | 3.1 ± 0.1 | 57.9 ± 0.5 |
| 2 | 3 | AGACCCACAGSGCAACCSACGGASA | 1.7 ± 0.2 | 60.9 ± 1.3 |

[a]S = Man$_9$-click-glycosylated EdU.
[b]$K_d$ and Fb$_{max}$ determined at RT by Nitrocellulose/PVDF filter binding assay, Fb$_{max}$ expressed as percentage.

Figure 1B:
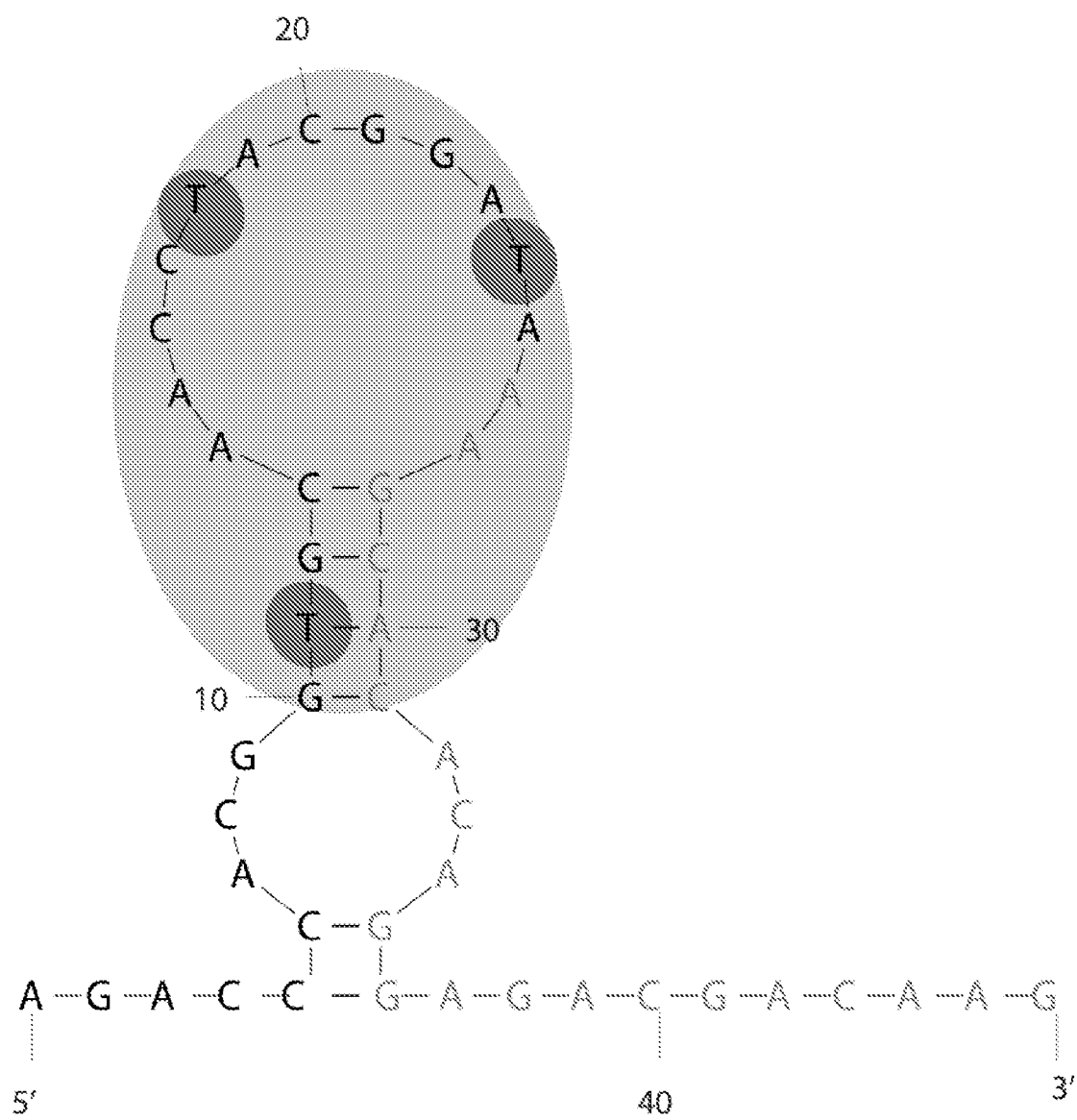
Figure 1C:
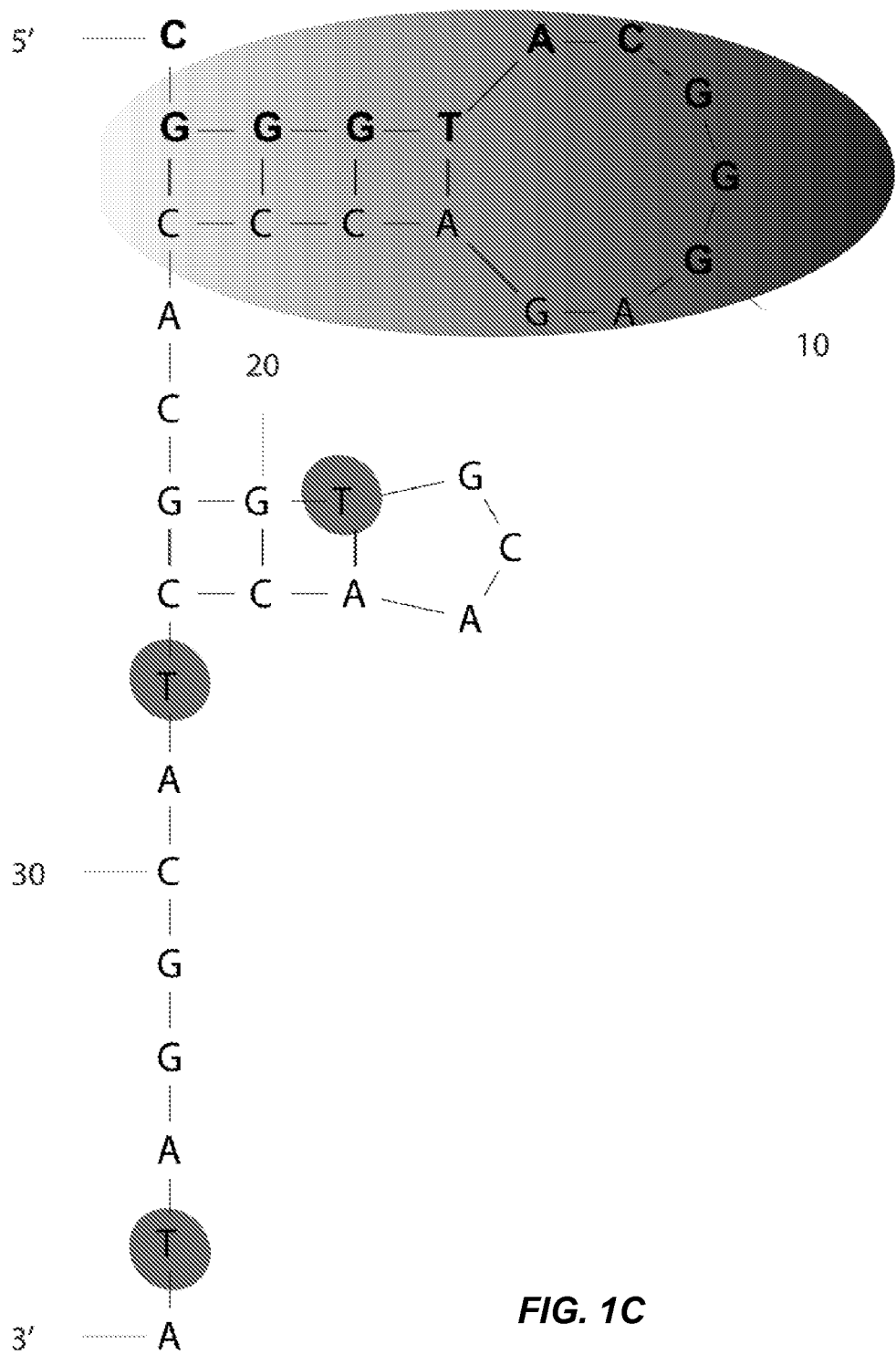
Figure 1D:
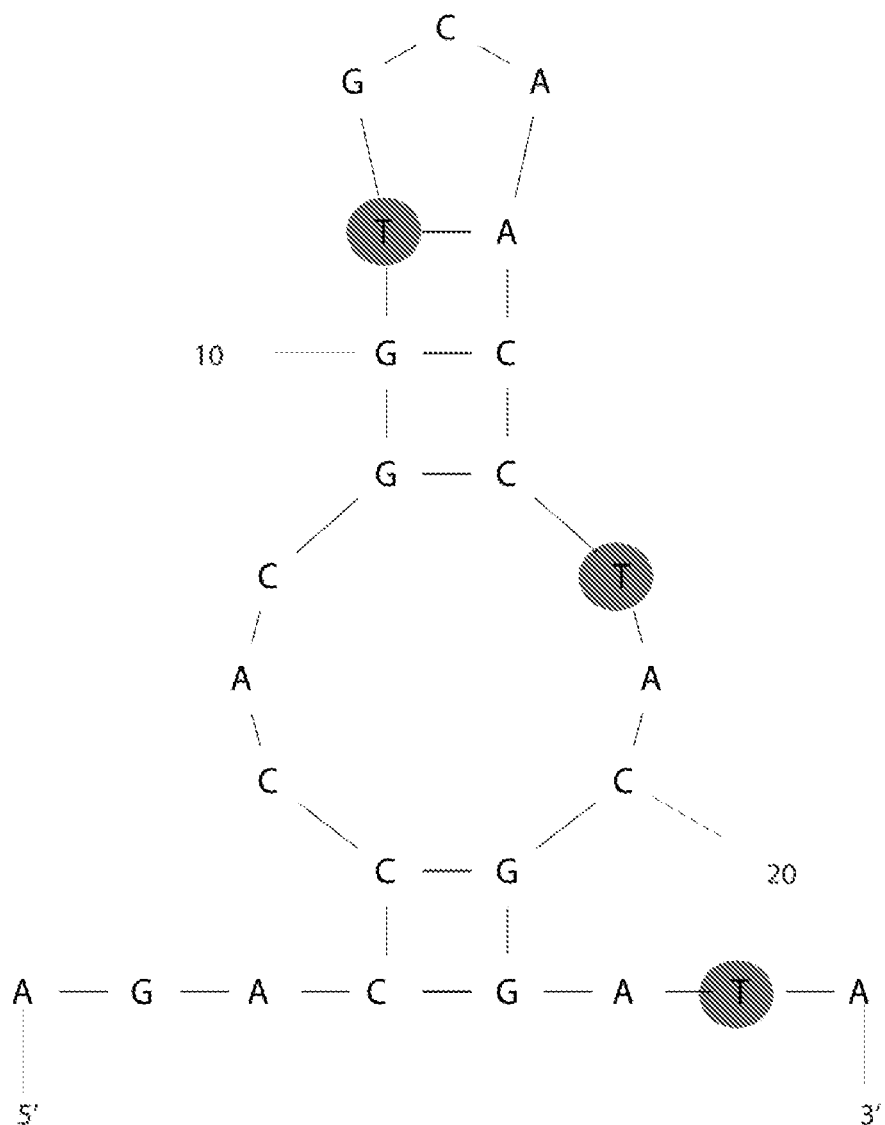
Figure 1E:
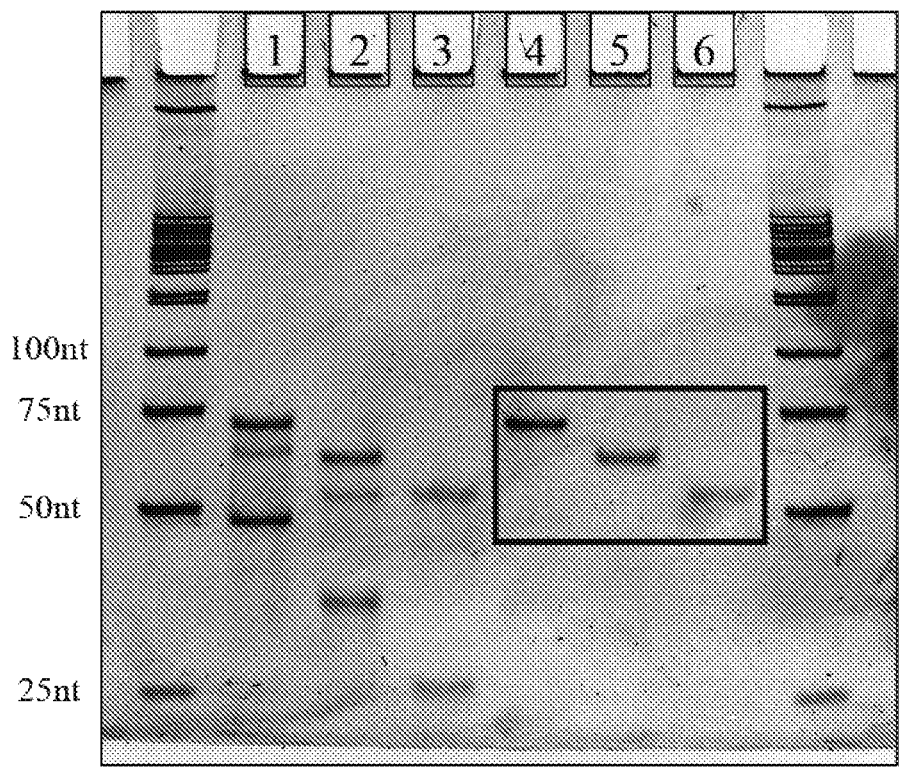
Figure 1F:
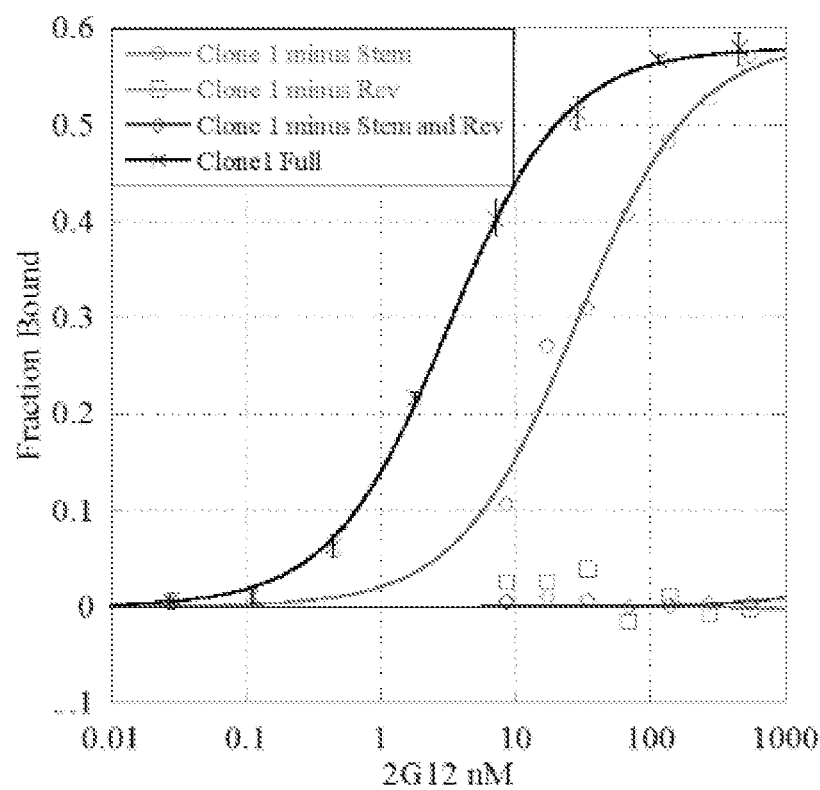

To gain a deeper understanding of the binding domain and structure of clone 1, a binding analysis was performed on a series of truncations. The full length clone 1 (SEQ ID NO: 7) was predicted by mFold analysis to fold into a structure containing two stem loops (FIG. 1A). The green 5' stem region formed a small hairpin having a 4 bp stem (shaded gradient gray). A second hairpin structure having a 4 bp stem (shaded gray) was predicted to form between the random region (black text) and the first 6 nucleotides of the reverse primer (gray text). This hairpin and stem contained all three of the glycosylation sites (shaded dark gray). The first truncations involved removal of the stem (FIG. 1B), removal of the reverse primer (FIG. 1C) and removal of both the stem and the reverse primer (FIG. 1D). If the yellow shaded hairpin structure had merit, the stem region truncation should not be massively detrimental to the binding whereas the reverse primer should be critical for binding due to the massive change in glycan spacing and arrangement. The truncations were synthesized and purified as shown in the gel in FIG. 1E. The binding of the truncations to 2G12 was then analyzed by filter-binding assay (data in Table 3, 1-B thru 1-D). The resulting binding curves (FIG. 1F) confirmed the complete loss of binding when the reverse primer was removed. The stem only truncation had a slightly higher $K_d$=24 nM when compared to the full sequence.

A more detailed truncation study was carried out to more fully understand the involvement of the reverse primer. The reverse primer was partially truncated (FIG. 2A, black bars) to see if the binding with 2G12 was perturbed. The truncated sequences T1-T4 in Table 3 were synthesized, purified and studied with the filter-binding assay (FIG. 2B). The results of this truncation study showed that the mFold analysis was likely correct in that the 3' overhang of the reverse primer was unnecessary for binding. To further test this result and to produce a more thermostable hairpin stem structure to be used in a vaccine trial, the 4 bp stem was extended (E1 thru E3 in Table 3). Sequences E1-E3 were predicted to fold into 6 bp, 9 bp and 13 bp stems to stabilize the hairpin loop (mFold analysis FIG. 3). All of these sequences bound to 2G12 with low nM affinity despite being mutated to accommodate the elongated stem region. This is strong evidence that the folding prediction is accurate. $Fb_{max}$ is a measure of the maximum fraction bound in the binding assay when the concentration of the antibody target is very high. E1 and E3 showed an improved $Fb_{max}$ of ~71% and ~74% respectively.

This work is important to the development of a vaccine for several reasons. First, the length of the DNA oligo can be minimized to decrease production cost. Second, the longer stem region of the hairpin loop makes the construct more rigid and less likely to unfold at physiological temperatures. Third, further enhancements to the structure can be made to render them serum stable. For example, variants of clones E1 and E3 will be prepared using either inverted oligo sequences or 2'-O-methyl-substituted nucleotides to stabilize them against nuclease activity. Fourth, the minimal glycoDNA is an ideal candidate for x-ray crystallization studies to investigate the structural binding with 2G12. The non-truncated clones bound tightly to 2G12, but clearly had a significant amount of extraneous DNA bases which would likely interfere in structural analysis and provide unnecessary sites for nuclease digestion of a vaccine candidate.

Example 2—Synthesis of Clone E1 Variant Using 2'-O-Methyl Substituted Nucleotides It has been shown that substitutions of purines (adenosine and guanosine) with 2'-methoxy deoxyribose purines can reduce or eliminate endonuclease degradation in serum. Because these modifications of DNA aptamers can affect the folding and binding of the clone, the 2'-methoxy substitutions of the purines should be incorporated systematically and tested for site specific tolerance. Clone E1 will be the subject of a site-specific mutagenesis study. The sequences of the clones to be prepared by solid-phase synthesis are shown in Table 4 below. Once the panel has been synthesized, the binding to 2G12 will be studied as described above. Sites within Clone E1 that are determined to tolerate the 2'-methoxy modification will be combined in a second-generation clone bearing multiple 2'-methoxy modifications. The binding of the advanced generation clone to 2G12 will be verified as previously described. Successful modifications obtained in Example 2 will be combined with the results of example 3.

TABLE 3

Clone 1 Truncations and Elongations

| Clone | SEQ ID NO: | Sequence[a] 5' stem region ... 3' reverse primer region | $K_d$ (nM)[b] | $Fb_{max}$[b] |
|---|---|---|---|---|
| 1 | 7 | CGGGTACGGGAGACCCACGGSGCAACCSACGGASAAAGCACACAGGAGACGACAAG | 5.5 ± 0.9 | 55.7 ± 1.2 |
| 1-B | 8 | AGACCCACGGSGCAACCSACGGASAAAGCACACAGGAGACGACAAG | 27.9 ± 4.2 | 58.5 ± 2.2 |
| 1-C | 9 | CGGGTACGGGAGACCCACGGSGCAACCSACGGASA | NB[c] | ND[c] |
| 1-D | 10 | AGACCCACGGSGCAACCSACGGASA | NB[c] | ND[c] |
| T1 | 11 | AGACCCACGGSGCAACCSACGGASAAAGCACAC | 8.4 ± 0.7 | 60.9 ± 0.9 |
| T2 | 12 | AGACCCACGGSGCAACCSACGGASAAAGCACACAGGAG | 13.3 ± 2.4 | 53.2 ± 2.5 |
| T3 | 13 | CGGGTACGGGAGACCCACGGSGCAACCSACGGASAAAGCACAC | 12.1 ± 2.0 | 44.2 ± 1.6 |
| T4 | 14 | CGGGTACGGGAGACCCACGGSGCAACCSACGGASAAAGCACACAGGAG | 11.9 ± 3.0 | 53.6 ± 3.5 |
| E1 | 2 | AGACCCACGGSGCAACCSACGGASAAAGCACCG | 7.5 ± 1.0 | 71.2 ± 2.4 |
| E2 | 4 | AGACCCTCGGSGCAACCSACGGASAAAGCACCGAGG | 10.2 ± 1.5 | 56.9 ± 2.1 |
| E3 | 6 | TGTCCCTCGGSGCAACCSACGGASAAAGCACCGAGGGACA | 11.9 ± 3.0 | 74.4 ± 4.9 |

Figure 2A:
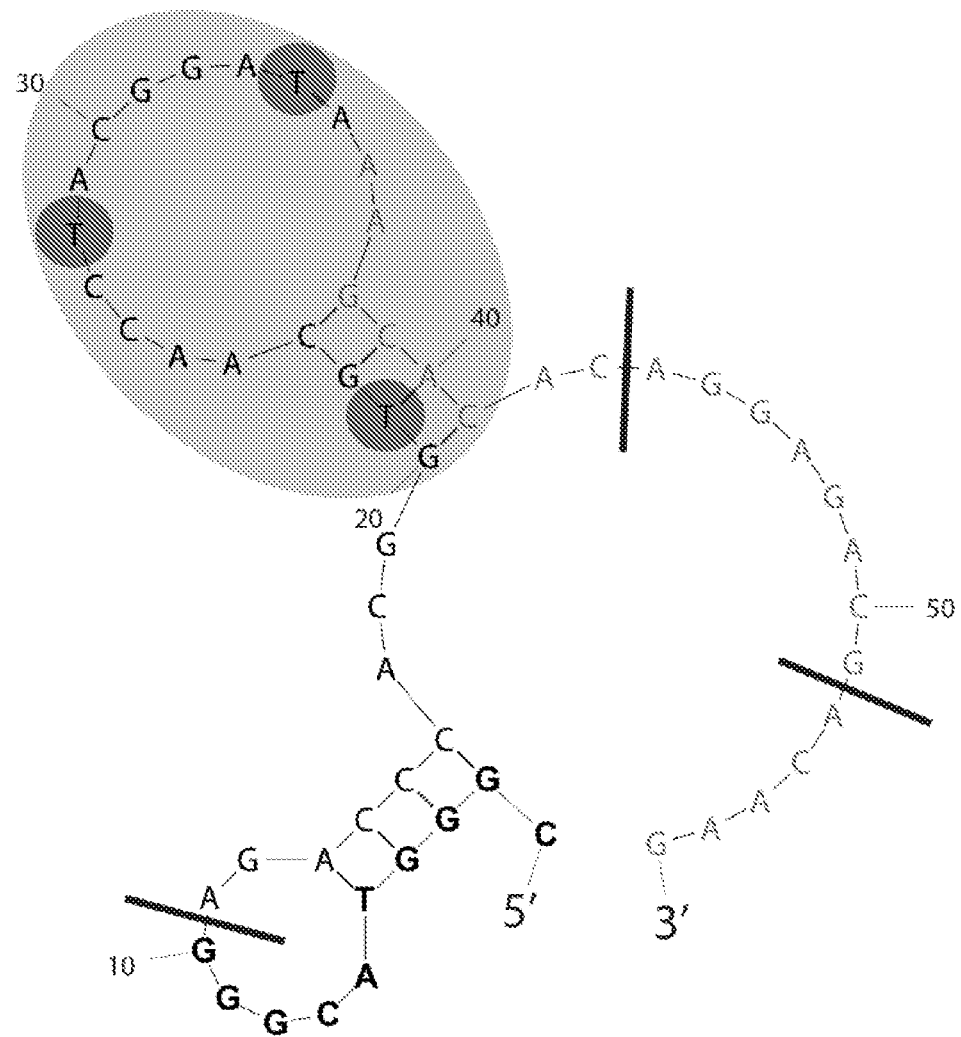
FIGS. 2A-B illustrate Clone 1 truncation sites (FIG. 2A, SEQ ID NO: 7) and 2G12 binding data for a series of truncations and elongations (FIG. 2B). As described in Table 3, infra at Example 1, T1 (SEQ ID NO: 11), T2 (SEQ ID NO: 12), T3 (SEQ ID NO: 13), T4 (SEQ ID NO: 14), E1 (SEQ ID NO: 2), E2 (SEQ ID NO: 4), and E3 (SEQ ID NO: 6) 2G12 binding data are graphically depicted in FIG. 2B.
Figure 3:
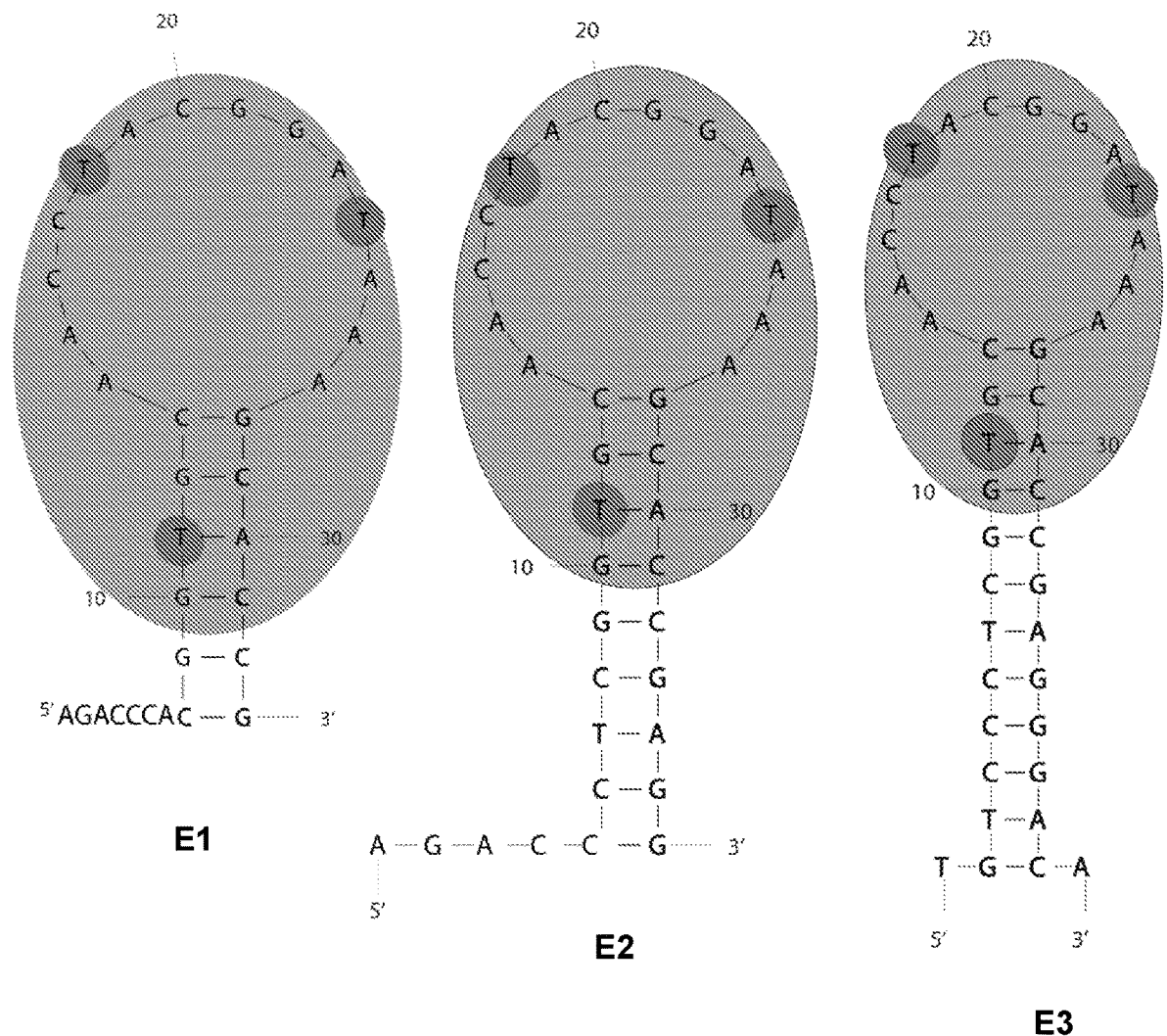
FIG. 3 illustrates a comparative mFold analysis on Clone 1 stem for extensions (E1, SEQ ID NO: 2) 6 bp stem, (E2, SEQ ID NO: 4) 9 bp stem, and (E3, SEQ ID NO: 6) 13 bp stem.

[a]S = Man₉-click-glycosylated EdU (same as depicted "T" in FIGS. 1A, 2A); italicized text in the 5' stem region forms part of the 5' stem/loop in Clone 1 (FIGS. 1A, 2A); non-italicized text in the 3' reverse primer region forms part of the reverse primer binding site in Clone 1 (FIGS. 1A, 2A); italicized text in the 3' reverse primer region are added nucleotides for the stem extension (FIG. 3). Bold underline is the predicted hairpin stem region as predicted by mFold (see, e.g., FIG. 3).
[b]$K_d$ and $Fb_{max}$ determined at room temperature by Nitrocellulose/PVDF filter binding assay, $Fb_{max}$ expressed as percentages.
[c]NB = no binding detected with up to 500 nM 2G12, ND = not determined.

TABLE 4

Clone E1 (SEQ ID NO: 2) With Purine 2'-Methoxy Mutation

| Clone | SEQ ID NO: | Sequence[a] |
|---|---|---|
| E1-M1 | 16 | AGACCCACGGSGCAACCSACGGASAAAGCACCG |
| E1-M2 | 17 | AGACCCACGGSGCAACCSACGGASAAAGCACCG |
| E1-M3 | 18 | AGACCCACGGSGCAACCSACGGASAAAGCACCG |
| E1-M4 | 19 | AGACCCACGGSGCAACCSACGGASAAAGCACCG |
| E1-M5 | 20 | AGACCCACGGSGCAACCSACGGASAAAGCACCG |
| E1-M6 | 21 | AGACCCACGGSGCAACCSACGGASAAAGCACCG |
| E1-M7 | 22 | AGACCCACGGSGCAACCSACGGASAAAGCACCG |
| E1-M8 | 23 | AGACCCACGGSGCAACCSACGGASAAAGCACCG |
| E1-M9 | 24 | AGACCCACGGSGCAACCSACGGASAAAGCACCG |
| E1-M10 | 25 | AGACCCACGGSGCAACCSACGGASAAAGCACCG |
| E1-M11 | 26 | AGACCCACGGSGCAACCSACGGASAAAGCACCG |
| E1-M12 | 27 | AGACCCACGGSGCAACCSACGGASAAAGCACCG |
| E1-M13 | 28 | AGACCCACGGSGCAACCSACGGASAAAGCACCG |
| E1-M14 | 29 | AGACCCACGGSGCAACCSACGGASAAAGCACCG |
| E1-M15 | 30 | AGACCCACGGSGCAACCSACGGASAAAGCACCG |
| E1-M16 | 31 | AGACCCACGGSGCAACCSACGGASAAAGCACCG |
| E1-M17 | 32 | AGACCCACGGSGCAACCSACGGASAAAGCACCG |
| E1-M18 | 33 | AGACCCACGGSGCAACCSACGGASAAAGCACCG |
| E1-M19 | 34 | AGACCCACGGSGCAACCSACGGASAAAGCACCG |

Figure 2B:
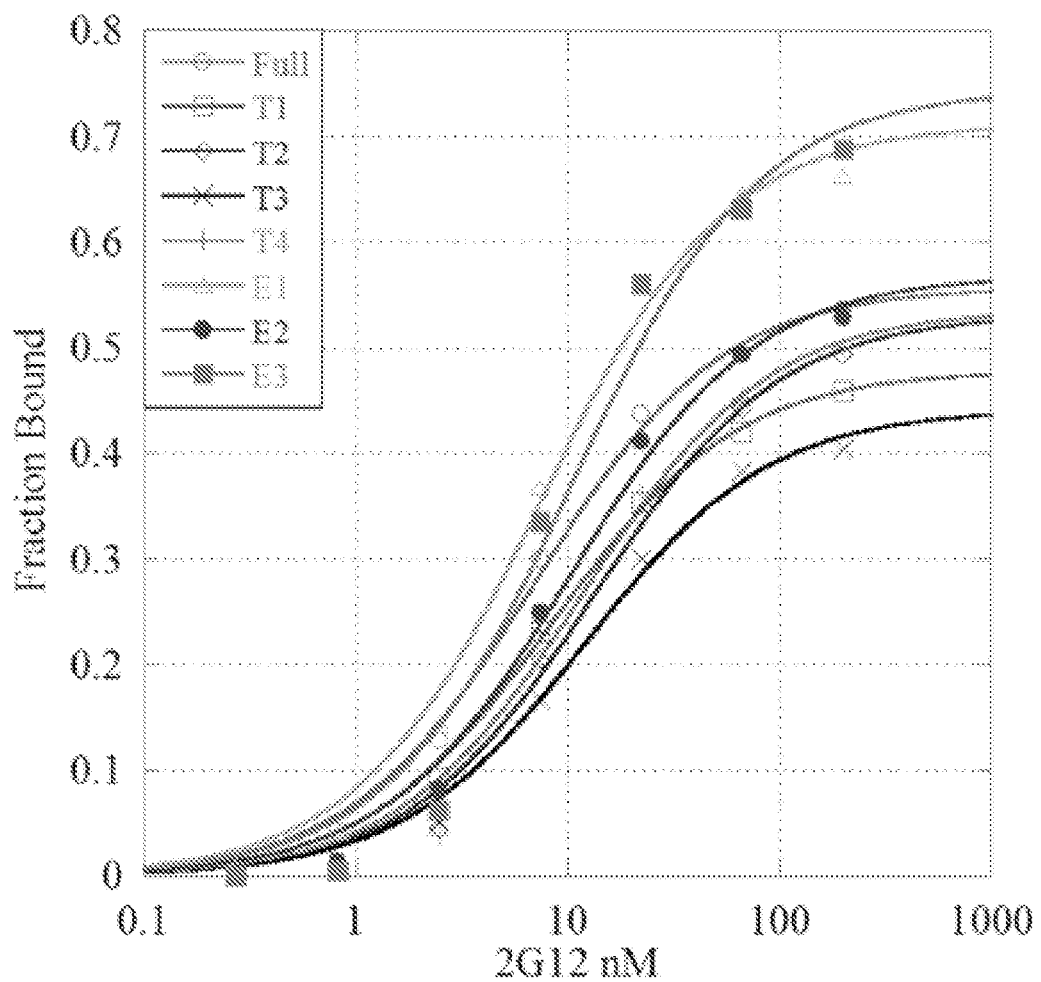

[a] S = Man$_9$-click-glycosylated EdU (same as depicted "T" in FIGS. 1A, 2A);
A = 2'-methoxy deoxyribose adenosine;
G = 2'-methoxy deoxyribose guanosine;
italicized text in the 3' reverse primer region forms part of the reverse primer binding site in Clone 1 (see FIGS. 1A, 2A); non-italicized text in the 3' reverse primer region are added nucleotides for the stem extension (see FIG. 3).
Bold underline is the predicted hairpin stem region as predicted by mFold (see, e.g., FIG. 3).

Example 3—Synthesis of Clone E1 Variant Using Inverted Oligonucleotides

Figure 4:
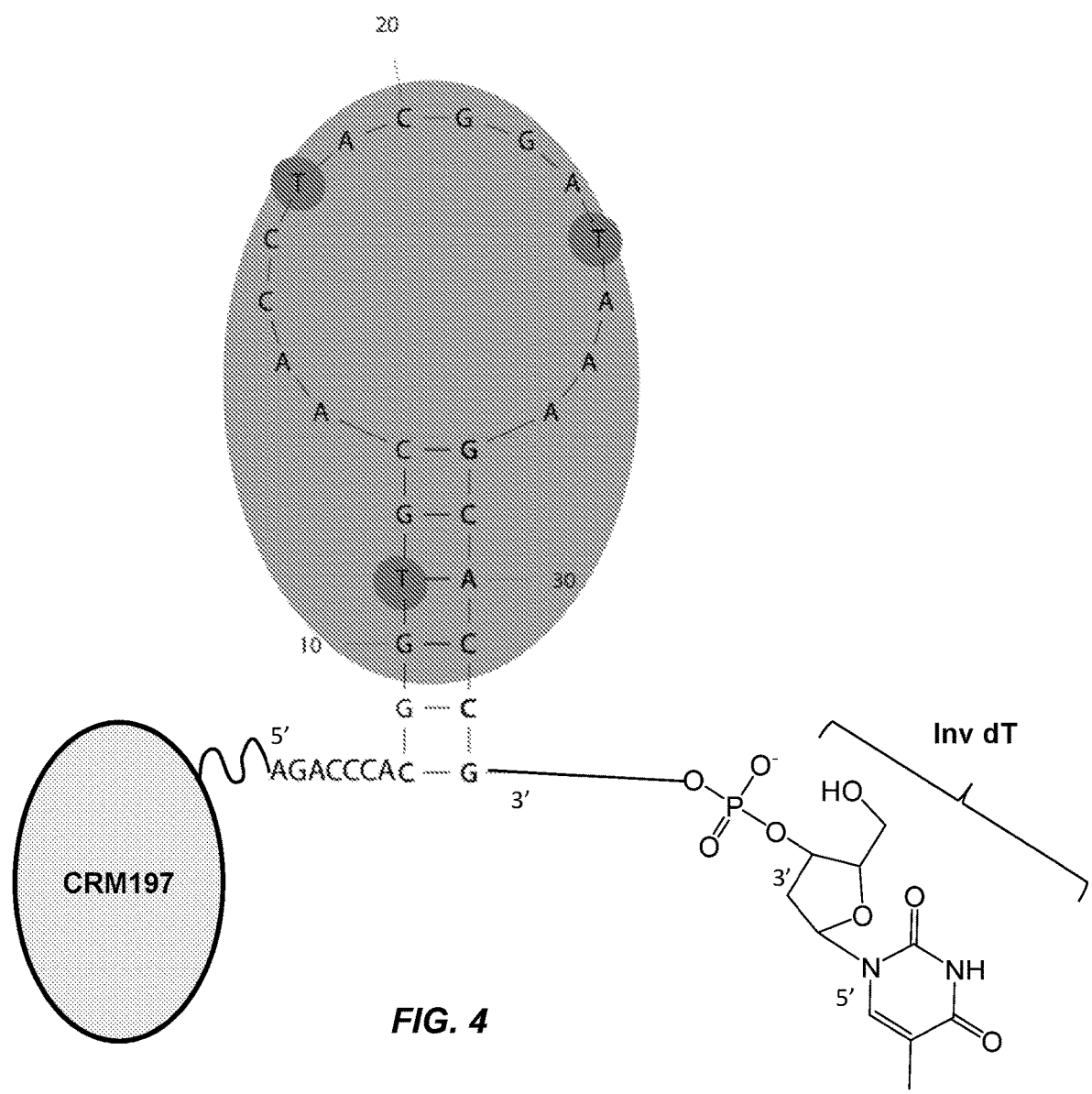
FIG. 4 illustrates schematically a conjugate of the invention that includes a 3'-inverted dT appended to the 3' terminus of the optimized 2'-O-methylated version of E1, and the immunogenic carrier CRM 197 appended to the 5' terminus thereof.

A 3'-inverted dT (see FIG. 4) will be appended to the optimized clone obtained from Example 2. The optimized clone will be synthesized on solid support and the cleaved modified DNA will be glycosylated and its binding to 2G12 will be tested as previously described. Having optimized the plasma stability of Clone E1, the 5' end of the clone will be modified with a thiol to facilitate the attachment of the clone to a maleimide modified carrier protein such as CRM197 (see FIG. 4).

The E1-CRM conjugate will then be formulated and intramuscularly administered into a naive rabbit population. Plasma from the rabbits will be taken during the course of the experiment and antibody serum titers against E1 and gp120 will be monitored by ELISA.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Specific aspects of the invention are identified below.

What is claimed:

1. An oligonucleotide that binds specifically to HIV neutralizing monoclonal antibody 2G12 with a $K_d$ value that is lower than 20 nM, the oligonucleotide comprising a predicted structure, at 37° C., having exactly one stem-loop whereby the loop comprises the nucleotide sequence of AACCNACGGANAAA (SEQ ID NO:1), where N is a modified nucleoside base, and the stem includes at least 3 nucleotide base-pairs and one of the nucleotides in the stem includes a modified nucleoside base, wherein the modified nucleoside base has the structure

-B-L-A where

A is a branched-chain $Man_9$ oligosaccharide,

L is a linker molecule, and

B is independently a pyrimidine or pyridine base linked to the sugar-phosphate backbone of the oligonucleotide.

2. The oligonucleotide according to claim 1, wherein the oligonucleotide binds specifically to the HIV neutralizing monoclonal antibody 2G12 with a $K_d$ value that is lower than 10 nM.

3. The oligonucleotide according to claim 1, wherein the oligonucleotide binds specifically to HIV neutralizing monoclonal antibody 2G12 with an $Fb_{max}$ value (in percent) that is greater than about 60.

4. The oligonucleotide according to claim 1, wherein each said modified nucleoside base comprises the structure according to formula (IV)

(IV)

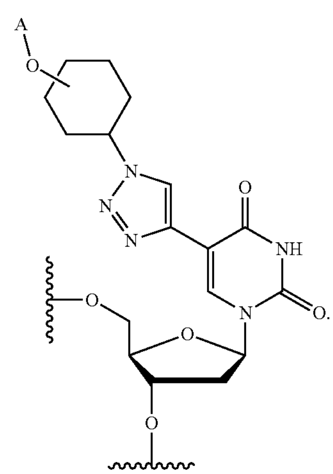

5. The oligonucleotide according to claim 1, wherein the one nucleotide in the stem including the modified nucleoside base is positioned in the third base pair of the stem, counting from the loop structure.

6. The oligonucleotide according to claim 1, wherein the stem includes at least 5 base-paired nucleotides, or at least 8 base-paired nucleotides.

7. An oligonucleotide that binds specifically to HIV neutralizing monoclonal antibody 2G12 with a $K_d$ value that is lower than 20 nM, the oligonucleotide comprising a predicted structure, at 37° C., having exactly one stem-loop whereby the loop comprises the nucleotide sequence of AACCNACGGANAAA (SEQ ID NO:1), where N is a modified nucleoside base, and the stem includes at least 3 nucleotide base-pairs and one of the nucleotides in the stem includes a modified nucleoside base, wherein the modified nucleoside base has the structure

-B-L-A where
- A is a branched-chain $Man_9$ oligosaccharide,
- L is a linker molecule, and
- B is independently a pyrimidine or pyridine base linked to the sugar-phosphate backbone of the oligonucleotide, and wherein the oligonucleotide comprises the sequence of

```
(E1)
AGACCCACGGNGCAACCNACGGANAAAGCACCG,
or (E1 nt 8-33)
CGGNGCAACCNACGGANAAAGCACCG,
or (E2)
AGACCCTCGGNGCAACCNACGGANAAAGCACCGAGG,
or (E2 nt 5-36)
CCTCGGNGCAACCNACGGANAAAGCACCGAGG,
or (E3)
TGTCCCTCGGNGCAACCNACGGANAAAGCACCGAGGGACA.
```

8. The oligonucleotide according to claim 1, wherein the oligonucleotide comprises one or more phosphorothioate-linked nucleotides, one or more inverted bases that afford a 3'-3' or 5'-5' reversed linkage, one or more 2'-fluoro-, 2'-amino, 2'-O-methyl-, 5'-iodo-, or 5'-bromo-modified nucleotides, or a combination thereof.

9. An immunogenic conjugate comprising an oligonucleotide according to claim 1 covalently or non-covalently bound to an immunogenic carrier molecule.

10. The immunogenic conjugate according to claim 9, wherein the immunogenic carrier molecule is selected from the group consisting of bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

11. A pharmaceutical composition comprising a pharmaceutically acceptable carrier and an oligonucleotide according to claim 1 or an immunogenic conjugate comprising the oligonucleotide covalently or non-covalently bound to an immunogenic carrier molecule.

12. The pharmaceutical composition according to claim 11 further comprising an adjuvant.

13. A method of inducing an immune response in an individual comprising:
administering to an individual an oligonucleotide according to claim 1 or an immunogenic conjugate comprising the oligonucleotide covalently or non-covalently bound to an immunogenic carrier molecule, wherein said administering is effective to induce an immune response against the oligonucleotide.

14. The method according to claim 13, wherein said administering is effective to induce a carbohydrate-binding, neutralizing antibody response.

15. The method according to claim 14, wherein the induced carbohydrate-binding, neutralizing antibody response is protective against HIV-1.

16. The method according to claim 13, wherein said administering is carried out orally, parenterally, subcutaneously, intravenously, intramuscularly, intraperitoneally, by intranasal instillation, by implantation, by intracavitary or intravesical instillation, intraarterially, intralesionally, transdermally, intra- or peri-tumorally, by application to mucous membranes, or by inhalation.

17. The method according to claim 13, wherein said administering is repeated.

18. The method according to claim 13, wherein the oligonucleotide or immunogenic conjugate is administered at a dose of about 1 μg to about 5 mg.

19. The method according to claim 13, wherein the individual is a human.

20. A method of inhibiting HIV-1 infection or proliferation comprising:
administering to an individual an oligonucleotide according to claim 1 or an immunogenic conjugate comprising the oligonucleotide covalently or non-covalently bound to an immunogenic carrier molecule, wherein said administering is effective to induce a neutralizing immune response against HIV-1.

21. A method for detecting a neutralizing antibody in serum comprising:
providing an oligonucleotide according to claim 1;
contacting the oligonucleotide with serum from an individual; and
detecting whether the oligonucleotide binds specifically to an antibody present in the serum, wherein said detecting is carried out using a label.

\* \* \* \* \*

UNITED STATES PATENT AND TRADEMARK OFFICE
CERTIFICATE OF CORRECTION

PATENT NO.       : 10,780,150 B2
APPLICATION NO.  : 16/092137
DATED            : September 22, 2020
INVENTOR(S)      : Krauss et al.

It is certified that error appears in the above-identified patent and that said Letters Patent is hereby corrected as shown below:

In the Claims

Claim 4, at Column 64, Lines 35-55: delete the structure shown and replace it with the following:

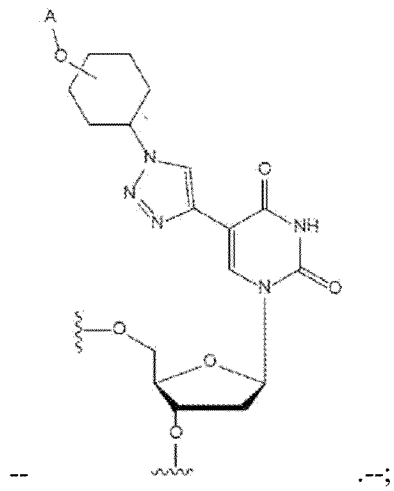

Claim 7, Column 65, Line 16: after "E1" and before the ")", insert --, SEQ ID NO:2--;

Claim 7, Column 65, Line 20: after "8-33" and before the ")", insert --, SEQ ID NO:3--;

Claim 7, Column 65, Line 23: after "E2" and before the ")", insert --, SEQ ID NO:4--;

Claim 7, Column 65, Line 26: after "5-36" and before the ")", insert --, SEQ ID NO:5--; and Claim 7, Column 65, Line 29: after "E3" and before the ")", insert --, SEQ ID NO:6--.

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*